US012424301B2

(12) United States Patent
Lee et al.

(10) Patent No.: US 12,424,301 B2
(45) Date of Patent: Sep. 23, 2025

(54) METHOD AND SYSTEM FOR PROVIDING GENETIC INFORMATION ANALYSIS RESULTS

(71) Applicant: Inocras Korea Inc., Daejeon (KR)

(72) Inventors: Jongkeun Lee, Goyang-si (KR); Seongyeol Park, Daejeon (KR); Youngoh Kwon, Incheon (KR)

(73) Assignee: Inocras Korea Inc., Daejeon (KR)

( * ) Notice: Subject to any disclaimer, the term of this patent is extended or adjusted under 35 U.S.C. 154(b) by 0 days.

(21) Appl. No.: 18/459,180

(22) Filed: Aug. 31, 2023

(65) Prior Publication Data
US 2024/0079094 A1 Mar. 7, 2024

(30) Foreign Application Priority Data

Sep. 5, 2022 (KR) .................. 10-2022-0112416
Dec. 5, 2022 (KR) .................. 10-2022-0167819

(51) Int. Cl.
| | | |
|---|---|---|
| G01N 33/48 | (2006.01) | |
| G16B 20/50 | (2019.01) | |
| G16B 30/10 | (2019.01) | |
| G16B 35/00 | (2019.01) | |
| G16B 45/00 | (2019.01) | |

(52) U.S. Cl.
CPC ............. *G16B 45/00* (2019.02); *G16B 20/50* (2019.02); *G16B 30/10* (2019.02); *G16B 35/00* (2019.02)

(58) Field of Classification Search
None
See application file for complete search history.

(56) References Cited

FOREIGN PATENT DOCUMENTS

| | | |
|---|---|---|
| KR | 10-2012-0042060 A | 5/2012 |
| KR | 10-2016-0099618 A | 8/2016 |
| KR | 10-2017-0019335 A | 2/2017 |
| KR | 10-1967248 B1 | 4/2019 |
| KR | 10-2020-0004204 A | 1/2020 |
| KR | 10-2021-0067529 A | 6/2021 |
| KR | 10-2021-0094783 A | 7/2021 |

OTHER PUBLICATIONS

Ferstay, Joel A., Cydney B. Nielsen, and Tamara Munzner. "Variant view: visualizing sequence variants in their gene context." IEEE transactions on visualization and computer graphics 19.12 (2013): 2546-2555.*
Huang, Po-Jung, et al. "Vanno: A Visualization-Aided Variant Annotation Tool." Human mutation 36.2 (2015): 167-174.*
Jia, Wenlong, et al. "Oviz-Bio: a web-based platform for interactive cancer genomics data visualization." Nucleic acids research 48. W1 (2020): W415-W426.*
Thorvaldsdottir, Helga, James T. Robinson, and Jill P. Mesirov. "Integrative Genomics Viewer (IGV): high-performance genomics data visualization and exploration." Briefings in bioinformatics 14.2 (2013): 178-192.*
Loraine, Ann E., and Gregg A. Helt. "Visualizing the genome: techniques for presenting human genome data and annotations." BMC bioinformatics 3 (2002): 1-8.*
Arakawa, Kazuharu, et al. "Genome Projector: zoomable genome map with multiple views." BMC bioinformatics 10 (2009): 1-10.*
Watkins, Xavier, et al. "ProtVista: visualization of protein sequence annotations." Bioinformatics 33.13 (2017): 2040-2041.*
Jaemoon Shin et al. "PhenGenVar: A User-Friendly Genetic Variant Detection and Visualization Tool for Precision Medicine" J. Pers. Med., 2022, pp. 1-11, vol. 12, No. 959.
Thomas M. Pearce et al. "Interactive Browser-Based Genomics Data Visualization Tools for Translational and Clinical Laboratory Applications" The Journal of Molecular Diagnostics, Nov. 2019, pp. 985-993, vol. 21, No. 6.
International Search Report issued in PCT/KR2023/010796; mailed Oct. 30, 2023.
The extended European search report issued by the European Patent Office on Jan. 31, 2024, which corresponds to European Patent Application No. 23194787.0-1126 and is related to U.S. Appl. No. 18/459,180.
Shin Jaemoon et al., "PhenGenVar: A User-Friendly Genetic Variant Detection and Visualization Tool for Precision Medicine", Journal of Personalized Medicine, vol. 12, No. 959, Jun. 12, 2022, pp. 1-11, XP093082442, doi: 10.3390/jpm12060959.
Anonymous, "Browsing Genomes with Ensembl / Coursebook v102", Jan. 26, 2021, pp. 1-60, XP93119941, https://ftp.ebi.ac.uk/pub/databases/ensembl/training/2021/OpenVirtualBrowser/Virtual_Browser_Ensembl_Coursebook.pdf.
Ensembl Training, "Virtual Workshop—The Ensembl Genome Browser—(2021): Webinar 3—Variation data and the VEP", YouTube video, Feb. 1, 2021, XP93120045, https://www.youtube.com/watch?v=6MItwC-ydN0.

* cited by examiner

*Primary Examiner* — Anna Skibinsky
(74) *Attorney, Agent, or Firm* — Studebaker Brackett PLLC

(57) ABSTRACT

Disclosed is a method of providing genetic information analysis results performed by at least one hardware processor. The method may include displaying a user interface configured to provide genetic information analysis results for a specimen. The user interface includes: a list of genes associated with a specific disease in a first region within the user interface; a first browser configured to visualize and search for information regarding a variant obtained from analysis of the specimen in a second region within the user interface; and a second browser configured to search for sequence information obtained from analysis of the specimen in a third region within the user interface. The method may further include displaying, in response to user input received through the user interface, interactive response information comprising details of the genetic information analysis results to at least one region within the user interface.

19 Claims, 28 Drawing Sheets

FIG. 13
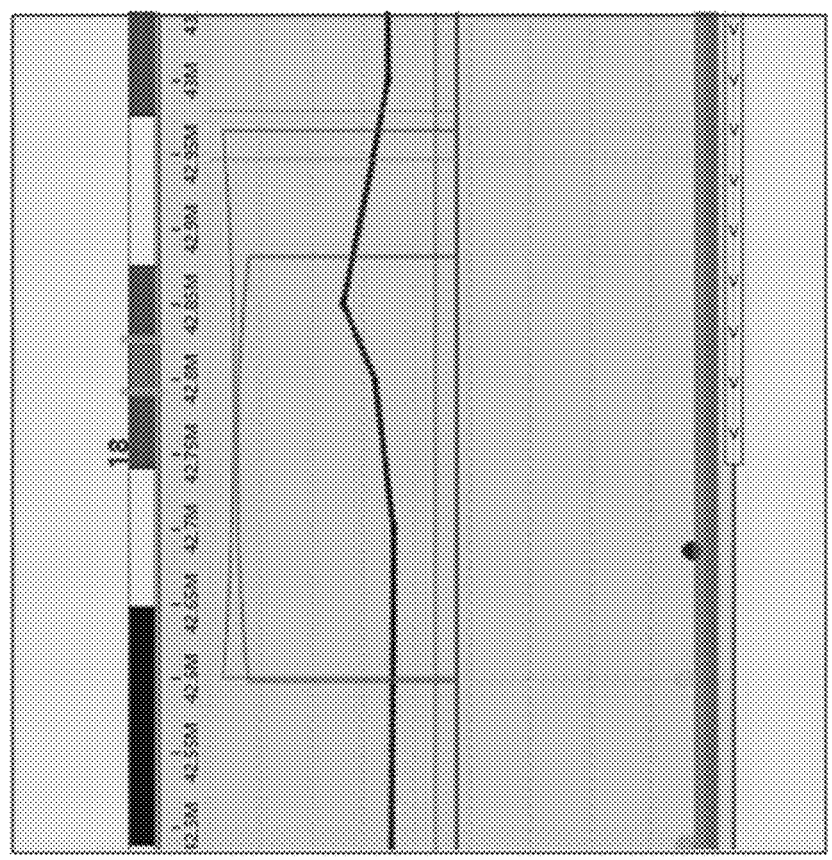
1320
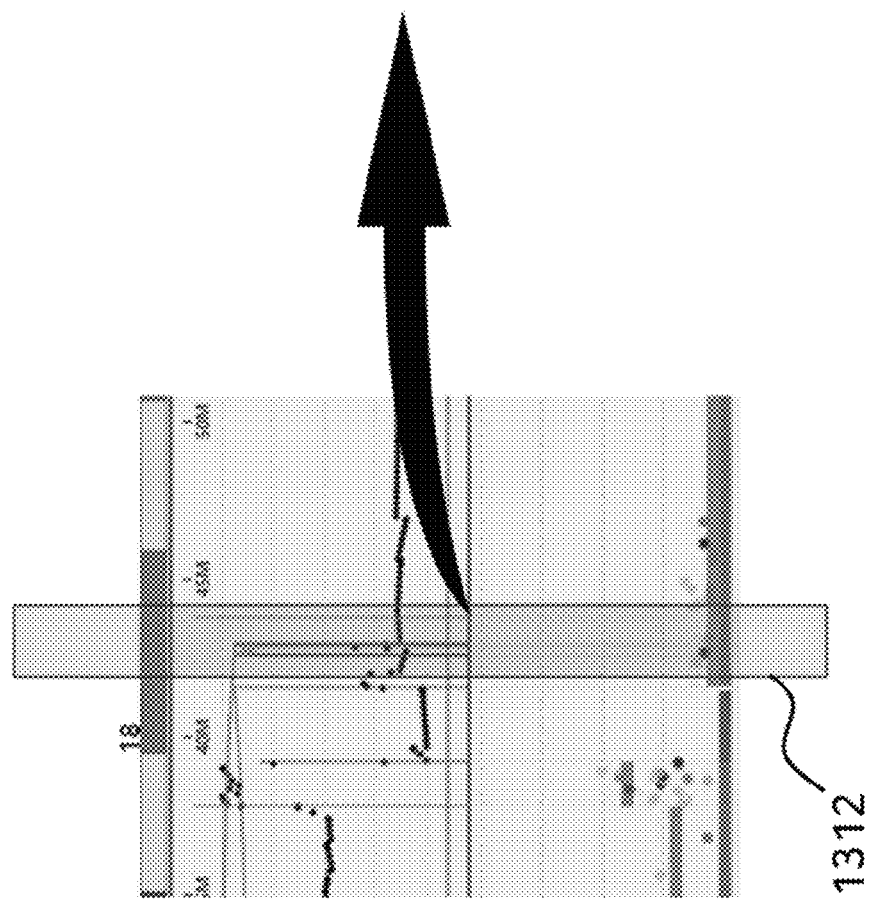
1310
1312

METHOD AND SYSTEM FOR PROVIDING GENETIC INFORMATION ANALYSIS RESULTS

CROSS-REFERENCE TO RELATED APPLICATIONS

The present application claims the benefit of priority to Korean Patent Application No. 10-2022-0112416, filed on Sep. 5, 2022, and Korean Patent Application No. 10-2022-0167819, filed on Dec. 5, 2022. The disclosures of the above-listed applications are hereby incorporated by reference herein in their entirety.

BACKGROUND

Field of the Invention

The present disclosure relates to a method of providing genetic information analysis results, and more particularly to a method and system for providing genetic information analysis results to a user using a user interface including a plurality of browsers.

Description of the Related Art

In recent years, research has been actively conducted to identify genes associated with human diseases. In particular, a project is actively underway to decode a whole genome, which contains genetic information of the human body, to create a genetic map, and to analyze the same, thereby predicting the occurrence of human diseases in advance or diagnosing diseases that have already occurred.

In order to predict or diagnose a disease, the project may involve comparing subjects' genomic sequences to a reference sequence to identify a subject's genomic sequence having a variant and deriving a disease correlation for the subject based on the identified genomic sequence.

In order to effectively realize the project, next-generation sequencing (NGS) technology is used. The next-generation sequencing technology performs sequencing by synthesis of fragmented DNA (deoxyribonucleic acid) to generate a large number of short sequences. For example, when next-generation sequencing is performed using a sequencing device from Illumina, a DNA fragment is read and an image file is generated with a base labeled with a fluorescent material. Subsequently, the fluorescent material included in the image file is converted into a sequence, which is a set of computer-readable characters, and the sequence is aligned (mapped) based on the reference sequence. As the result of comparing the aligned sequence to the reference sequence, the location and gene where mutation occurred are identified.

A report predicting a human disease based on the location and gene where the mutation occurred is generated and provided to a medical professional, who may predict a subject's disease early based on the report or may develop an appropriate treatment plan through accurate diagnosis of the subject's disease.

Meanwhile, the medical professional may check the detailed analysis results and/or relevant data underlying the report in order to develop a more accurate treatment plan. In this case, the medical professional may access a database to retrieve patient-related data. For example, in order to check both analysis data for a specific chromosome and genetic information associated with the specific chromosome, the medical professional must access the database and manually search therefor. At this time, the medical professional may retrieve that data through search queries.

This way of the medical professional accessing the database and obtaining necessary data may reduce work efficiency and convenience of the medical professional.

Meanwhile, there are applications that provide a part the detailed analysis results and/or the relevant data on which the report is based. However, these applications provide only fragmented or uniform detailed data and do not provide a variety of information required by the medical professional.

SUMMARY

The present disclosure provides a method of providing genetic information analysis results, a computer program stored on a recording medium, and an apparatus (system) capable of solving the above problems.

The present disclosure may be implemented in a variety of ways, including a method, an apparatus (system), and/or a computer program stored on a computer-readable recording medium.

In accordance with an aspect of the present disclosure, the above and other objects can be accomplished by the provision of a method of providing genetic information analysis results performed by at least one hardware processor, the method including displaying a user interface configured to provide genetic information analysis results for a specimen. The user interface includes: a list of genes associated with a specific disease in a first region within the user interface; a first browser configured to visualize and search for information regarding a variant obtained from analysis of the specimen in a second region within the user interface; and a second browser configured to search for sequence information obtained from analysis of the specimen in a third region within the user interface. The method may further include displaying, in response to user input received through the user interface, interactive response information comprising details of the genetic information analysis results to at least one region within the user interface.

A non-transitory computer-readable recording medium storing a computer program being executed by a hardware processor to perform the method of providing genetic information analysis results.

In accordance with another aspect of the present disclosure, there is provided a computing device including a hardware memory; a display; and at least one hardware processor connected to the hardware memory, and configured to execute at least one computer-readable program stored in the hardware memory. The at least one hardware processor is configured to: control the display to display a user interface configured to provide genetic information analysis results for a specimen. The user interface comprises: a list of genes associated with a specific disease in a first region within the user interface; a first browser configured to visualize and search for information regarding a variant obtained from analysis of the specimen in a second region within the user interface; and a second browser configured to search for sequence information obtained from analysis of the specimen in a third region within the user interface. The at least one hardware processor is further configured to: control the display to display, in response to user input received through the user interface, interactive response information comprising details of the genetic information analysis results to at least one region within the user interface.

TECHNICAL IMPROVEMENT

According to some embodiments of the present disclosure, a user interface displayed on a screen of a device may provide interactive response information comprising details of the genetic information analysis results. Such embodiments as a whole integrates the genetic information analysis into a practical application. Specifically, such embodiments provide a specific technical improvement over prior art systems by providing interactive response information comprising details of the genetic information analysis results. The user interface capable of interactively inquiring about and searching for a large amount of genetic information analysis results may be provided. It results in improved data management. Thus, the efficiency and accuracy of data management may be improved.

Further, according to some embodiments of the present disclosure, a first browser configured to visualize and search for information regarding a variant obtained from analysis of the specimen in a second region within the user interface, and a second browser configured to search for sequence information obtained from analysis of the specimen in a third region within the user interface, are provided by a user interface displayed on a screen of a device. In response to a user input received through the above user interface, interactive response information comprising details of the genetic information analysis results to at least one region within the user interface is displayed. Such embodiments as a whole integrates the genetic information analysis into a practical application. Specifically, such embodiments provide a specific technical improvement over prior systems, resulting in that various kinds of information associated with genetic information analysis results may be efficiently provided through a plurality of regions included in a user interface. Thus, the efficiency and accuracy of data analysis may be improved.

Additionally, an ordered combination of the operations of some embodiments of the present disclosure demonstrate an improvement to the computer's ability to display information and interact with the user. Such ordered combination of the operations of some embodiments of the present disclosure further demonstrate that the embodiments are particular applications of and an improvement to the technology of providing genetic information analysis results, rather than well-understood, routine, conventional activity or a simple instruction to apply the abstract idea of generating genetic information analysis results or to perform the abstract idea on a generic set of computers.

BRIEF DESCRIPTION OF THE DRAWINGS

Embodiments of the present disclosure will be described with reference to the accompanying drawings, which are described below, wherein like reference numerals indicate like elements, but are not limited to, in which:

FIG. 13 is a view showing a further example of graphic object processing when graphic objects associated with structural variants are dense;

DETAILED DESCRIPTION

Figure 1:
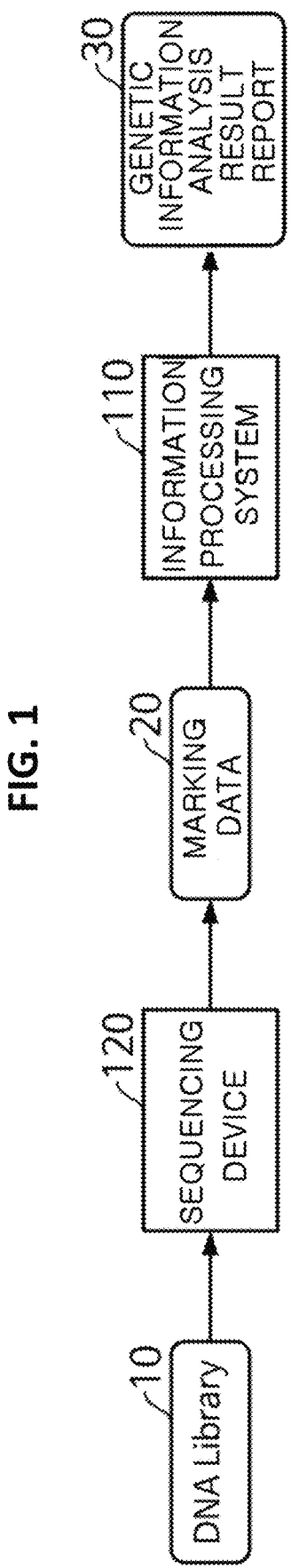
FIG. 1 is an illustrative view for schematically describing an information processing system according to an embodiment of the present disclosure and a service provision environment thereof.

Hereinafter, the details for implementing the present disclosure will be described in detail with reference to the accompanying drawings. In the following description, however, detailed descriptions of widely known functions or configurations will be omitted if the same unnecessarily obscures the gist of the present disclosure.

In the accompanying drawings, the same or corresponding elements are denoted by the same reference numerals. Also, in the following description of embodiments, duplicate descriptions of the same or corresponding elements may be omitted. However, omission of a description of an element is not intended to prevent such an element from being included in a certain embodiment.

Advantages and features of disclosed embodiments and methods of achieving the same will become apparent upon reference to the accompanying drawings and embodiments hereinafter described. However, the present disclosure is not limited to the embodiments hereinafter disclosed and may be implemented in many different forms. The embodiments are provided only to make the present disclosure complete and to make the scope of the invention fully known to those skilled in the art.

The following is a brief description of the terminology used herein, followed by a detailed description of the disclosed embodiments. The terminology used herein has been chosen to be as generic as possible in current common usage while taking into account functions of the disclosure, but may vary depending on the intent or precedent of those skilled in the art, the emergence of new technologies, etc. Also, in certain cases, terms are chosen arbitrarily by the applicant, and meaning thereof will be explained in detail in the description of the invention. Accordingly, terms used in the present disclosure should be defined based on meaning thereof and the context of the present disclosure as a whole, not merely on the name of the term.

In this specification, singular expressions include plural expressions unless the context clearly indicates that the singular expressions are singular. In addition, plural expressions include singular expressions unless the context clearly indicates that the plural expressions are plural. When a part is said to include an element throughout the specification, this means that the part may further include another element, not excluding the other element, unless particularly mentioned.

In addition, the term "module" or "unit" used in the specification refers to a software or hardware element, wherein the "module" or "unit" performs certain roles. However, the "module" or "unit" does not mean software- or hardware-specific. The "module" or "unit" may be configured to reside on an addressable storage medium and may be configured to reproduce one or more processors. As an example, therefore, the "module" or "unit" may include at least one of elements, such as software elements, object-oriented software elements, class elements, and task elements, processes, functions, attributes, procedures, subroutines, segments of program code, drivers, firmware, microcode, circuits, data, databases, data structures, tables, arrays, or variables. Elements and "modules" or "units" may be combined into fewer elements and "modules" or "units" or may be further separated into additional elements and "modules" or "units".

According to an embodiment of the present disclosure, the "module" or "unit" may be implemented by a processor and memory. The "processor" should be interpreted broadly to include a general purpose processor, a central processing unit (CPU), a microprocessor, a digital signal processor (DSP), a controller, a microcontroller, and a state machine. In some environments, the "processor" may also refer to an application-specific integrated circuit (ASIC), a programmable logic device (PLD), or a field-programmable gate array (FPGA). For example, the "processor" may also refer to a combination of processing devices, such as a combination of a DSP and a microprocessor, a combination of a plurality of microprocessors, a combination of one or more microprocessors combined with a DSP core, or a combination of any other configurations. In addition, the "memory" should be interpreted broadly to include any electronic component capable of storing electronic information. The "memory" may also refer to various types of processor-readable media, such as random access memory (RAM), read-only memory (ROM), non-volatile random access memory (NVRAM), programmable read-only memory (PROM), erasable programmable read-only memory (EPROM), electrically erasable PROM (EEPROM), flash memory, magnetic or marked data storage, and a register. When the processor can read information from the memory and/or write information to the memory, the memory is said to be in electronic communication with the processor. The memory integrated into the processor is in electronic communication with the processor.

In the present disclosure, a "system" may include, but is not limited to, at least one of a server device and a cloud device. For example, the system may be constituted by one or more server devices. As another example, the system may be constituted by one or more cloud devices (e.g., sequencing devices). As a further example, the system may be operated in a state of being constituted by a sever device and a cloud device.

In addition, the terms "first", "second", "A", "B", "(a)", "(b)", and the like used in the following embodiments are used to distinguish one element from another and are not intended to define the nature, sequence, or order of the element.

In addition, when one element is described as being "connected", "coupled", or "linked" to another element in the following embodiments, this should be understood as meaning that the element may be directly connected or linked to the other element or that a further element may be "connected", "coupled", or "linked" between the elements.

Furthermore, the term "comprises" and/or "comprising" used in the following embodiments does not exclude the presence or addition of one or more other elements, steps, operations, and/or devices.

Before describing various embodiments of the present disclosure, the terminology used herein will be described.

In embodiments of the present disclosure, a "graphic element" may be graphically based data including at least one of shapes, colors, and text. For example, a specific graphic element may be a specific shape, a specific color, and/or a specific text.

In embodiments of the present disclosure, a "graphic object" may consist of at least one graphic element, which may be graphically based information that is visually identifiable by a user. For example, a graphic object may be implemented as a specific shape with a specific color. For example, a first graphic object may be a first shape with a first color and a first size, and a second graphic object may be a second shape with a second color and a second size.

In embodiments of the present disclosure, "genetic information analysis results" may refer to the results of analysis of a whole genome or a part of the genome (e.g., a specific chromosome, a specific gene, or a target panel). It should be noted that, in the embodiments of the present disclosure, analysis information for a whole genome, analysis information for a specific chromosome, analysis information for a specific gene, and analysis information for a target panel are referred to as "genome analysis information" without distinguishing therebetween for ease of description.

In embodiments of the present disclosure, a "first browser" may refer to an application for searching for and exploring variants within genome analysis information. In some embodiments, the first browser may provide a view of variants found across the entire region of a whole genome.

In embodiments of the present disclosure, a "second browser" may refer to an application for searching for and exploring genome sequence information obtained as the result of genome analysis, for example, at a gene-by-gene level. Here, the sequence information may include a ribonucleic acid (RNA) sequence to which some regions of a DNA sequence have been transcribed by a transcription model and/or an amino acid sequence translated in response to such a sequence.

The first browser and/or the second browser may be implemented using various programming tools, such as JavaScript, Hypertext Markup Language (HTML), and an Application Programming Interface (API).

In embodiments of the present disclosure, a "base" is a unit constituting a base sequence or a nucleotide sequence and may be a component of a nucleotide. For example, the base may be represented by any one of "A" for adenine, "C" for cytosine, "G" for guanine, and "T" for thymine.

In embodiments of the present disclosure, a "base sequence" may be an arrangement of a plurality of bases. The base sequence may cover more than one chromosomes.

In embodiments of the present disclosure, a "variant" may be identified as the part of a specimen's base sequence that differs from a reference sequence. Here, the variant may refer to a mutation. In addition, the variant may refer to addition, change, and/or deletion of the base sequence for any reason (e.g., DNA damage or replication error).

In embodiments of the present disclosure, a "DNA library" is a genetic. A "DNA library" may be processed and prepared for analysis by a sequencing device. The DNA library may include countless DNA fragments obtained from cells (i.e., specimens) of one or more subjects.

In embodiments of the present disclosure, a "marking code" may be code associated with a base included in the DNA fragment. In an embodiment, the marking code may be image data. When the marking code is labeled, attributes of the marking code may be used. According to some embodiments, fluorescent materials that are distinct from each other may be used as an attribute of the marking code. For example, a first marking code may be labeled with a first fluorescent material representing adenine, and a second marking code may be labeled with a second fluorescent material representing cytosine. As another example, a third marking code may be labeled with a third fluorescent material representing guanine, and a fourth marking code may be labeled with a fourth fluorescent material representing thymine.

In embodiments of the present disclosure, "marking data" may be data including one or more marking codes. For example, the marking data may be an image file.

Hereinafter, various embodiments of the present disclosure will be described in detail with reference to the accompanying drawings.

FIG. 1 is an illustrative view for schematically describing an information processing system 110 according to an embodiment of the present disclosure and a service provision environment thereof. First, a DNA library 10 including a DNA sample of a subject may be generated. For example, pretreatment, such as collection of a cell (i.e., a specimen) of a subject (e.g., a patient) to be analyzed and heating and centrifugation of the cell in a state of being stored in a test tube with a predetermined solution, may be performed, whereby a DNA library 10 including countless DNA fragments obtained from the subject's cell may be generated.

The DNA library 10 may include only a DNA sample obtained from one subject, but typically includes DNA samples obtained from a plurality of subjects. For example, both a DNA sample generated from a cell of a first subject and a DNA sample generated from a cell of a second subject may be included in the DNA library 10. That is, sequencing operations on two or more subjects may be simultaneously performed by a sequencing device 120 at one time.

In some embodiments, the information processing system 110 collects information from a network of a medical data institution containing DNA information of one or more subjects, to configure the DNA library 10. The information processing system 110 comprises a local computer generating network access requests for individual controlled access network accounts, which may be managed by the medical data institutions; at least one filtering scheme; a plurality of sets of logical filtering elements; and a server coupled to the local computer and the network, the server associating each of the network accounts to at least one filtering scheme and at least one set of filtering elements, the server further receiving the network access requests from the local computer and executing said associated filtering scheme utilizing said associated set of logical filtering elements, to selectively collect information for configuring the DNA library 10. These embodiments having an ordered combination of filtering operations provide a technology-based solution of filtering medical data collected from the Internet network, that overcomes the disadvantages of prior art filtering systems.

The DNA library 10 may be loaded into a flow cell, and the flow cell may be introduced into the sequencing device 120. In some embodiments, any method for introducing the DNA library 10 into the sequencing device 120 may be used.

The sequencing device 120 may identify the base type of each DNA fragment included in the DNA library 10, and may generate marking data including a marking code corresponding to the identified base type. According to an embodiment, the sequencing device 120 may update marking data at each cycle by identifying one base included in each DNA fragment, generating a marking code corresponding to the identified base, and further writing the generated marking code to the marking data. At each cycle, the sequencing device 120 may generate a single image file representing marking codes generated for all DNA fragments. The marking data may be a set of image files generated at each cycle, and may be stored in a storage device which the information processing system 110 can access. After a certain number of cycles (e.g., 300 cycles), marking data 20 including marking codes generated in all of the cycles may be generated. According to an embodiment, a plurality of marking data 20 corresponding to the number of DNA fragments may be generated by the sequencing device 120.

The information processing system 110 may be a system that analyzes a base sequence and outputs, or displays, a genetic information analysis result report 30 including the analyzed results. For example, when generation of marking data 20 by the sequencing device 120 is completed, the information processing system 110 may generate a base sequence based on the marking data 20. According to an embodiment, a plurality of marking data 20 corresponding to the number of DNA fragments may be generated by the sequencing device 120, and the information processing system 110 may generate a base sequence including a number of reads corresponding to the number of DNA fragments. For example, when n DNA fragments (where n is a natural number) are included in the DNA library 10, the sequencing device 120 may generate n pieces of marking data 20 at a specific cycle. Subsequently, the information processing system 110 may generate a base sequence for a specimen including n reads based on the n pieces of marking data 20.

Although an embodiment in which the sequencing device 120 outputs marking data 20 and the information processing system 110 generates a base sequence from the marking data 20 was described in the above, the sequencing device 120 may output the base sequence (e.g., a FASTQ file) instead of the marking data 20 in other embodiments.

In addition, the information processing system 110 may identify a plurality of variants found in the specimen by comparing the base sequence for the specimen to a reference sequence, aligning the base sequence for the specimen, and comparing the difference between the aligned base sequence and the reference sequence. The information processing system 110 may generate a genetic information analysis result report 30 including genetic information analysis results based on the plurality of variants found in the specimen. For example, the genetic information analysis result report 30 may include the genetic information analysis results and any information associated therewith. For example, the genetic information analysis result report 30 may include, but is not limited to, the location of mutations found in the specimen, the type of each mutation, statistical information about the analysis results, information related to tumor mutational burden (TMB), and information related to mutation signature. In addition, the genetic information analysis result report 30 may further include information about a patient from whom the specimen was collected, a list of drivers associated with a specific disease, and details about the mutated gene.

Here, the genetic information analysis result report 30 may be provided to a user (e.g., medical staff) using a user interface, as described below. Here, the user interface, which is a means configured to conveniently provide the results of analysis of the base sequence, may provide the user with interactive response information including details of the genetic information analysis results based on user input. For example, when the user selects a specific mutation, chromosome and gene information associated with the mutation may be output through the user interface.

The user interface may be output to a display means included in or connected to the information processing system 110, and information related to genome analysis may be output through the user interface. As another example, the information processing system 110 may transmit the information related to genome analysis to a user terminal over a network, and the user terminal may output the received information related to genome analysis through the user interface.

In some embodiments, the information processing system 110 may automatically generate a message containing the genetic information analysis result report 30, in response to user input received through the user interface, and may transmit the message to all of external devices being connected with the information processing system 110, via a network, so that each external device has immediate access to the genetic information analysis result report 30.

In some embodiments, the information processing system 110 may share a screen with the external devices, in real-time. In these embodiments, the information processing system 110 may control the external devices to display the same screen on their respective screens as a shared screen. Each of the information processing system 110 and the external devices may have an operation right switching function configured to acquire an operation right, a transmission data generating function configured to generate transmission data including operational information of an input operation, and a drawing function configured to draw a display object on the screen.

In some embodiments, the external devices may include a medical device, a user device, a guardian device, and a hospital device, a medical research device, and a pharmacy device.

In some embodiments, a pharmacy device may automatically generate a prescription according to the genetic information analysis result report 30, and the information processing system 110 may receive such the prescription. In some embodiments, the pharmacy device may automatically instruct a delivery company's server to initiate a delivery for medicines according to the prescription.

In some embodiments, a medical research device may perform analysis of the genetic information analysis result report 30 by using machine learning data, and the information processing system 110 may receive analysis result data.

Figure 2:
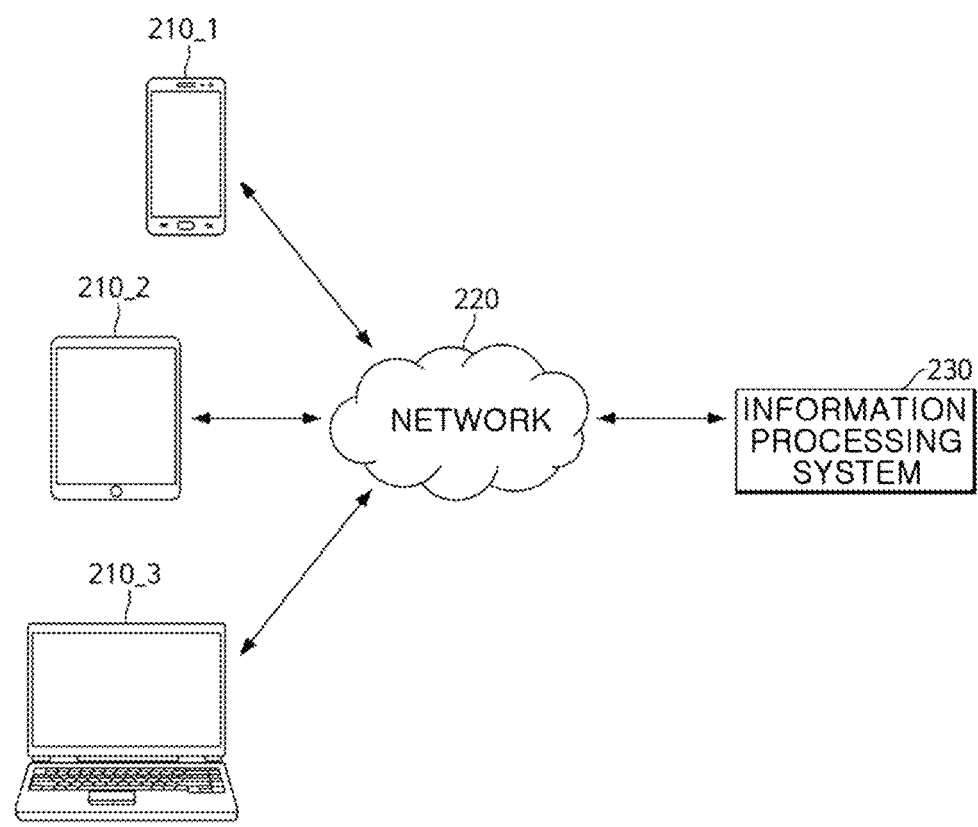
FIG. 2 is a schematic view illustrating a configuration in which an information processing system according to an embodiment of the present disclosure is communicably connected to a plurality of user terminals.

FIG. 2 is a schematic view illustrating a configuration in which an information processing system 230 according to an embodiment of the present disclosure is communicably connected to a plurality of user terminals 210_1, 210_2, and 210_3. As shown, the plurality of user terminals 210_1, 210_2, and 210_3 may be connected to the information processing system 230 capable of providing genetic information analysis results of a specimen over a network 220. For example, the information processing system 110 of FIG. 1 may be the same system as the information processing system 230 of FIG. 2.

In an embodiment, the information processing system 230 may include one or more server devices and/or databases capable of storing, providing, and executing a program (e.g., a downloadable application) configured to execute a genetic information analysis service, etc. and data or one or more distributed computing devices and/or distributed databases based on a cloud computing service. In an embodiment, the genetic information analysis service provided by the information processing system 230 may be provided to a user via a genetic information analysis service-related application or the like installed on each of the plurality of user terminals 210_1, 210_2, and 210_3. For example, the information processing system 230 may transmit a part or the entirety of the genetic information analysis result report to the user terminals 210_1, 210_2, and 210_3, and each of the user terminals 210_1, 210_2, and 210_3 may output data included in the genetic information analysis result report via a user interface.

The plurality of user terminals 210_1, 210_2, and 210_3 may be computing devices capable of communicating with the information processing system 230 over the network 220.

The network 220 may be configured to enable communication between the plurality of user terminals 210_1, 210_2, and 210_3 and the information processing system 230. Depending on the installation environment, the network 220 may be constituted by a wired network, such as Ethernet, a wired home network (power line communication), a telephone line communication device, or RS-serial communication, a wireless network, such as a mobile communication network, wireless LAN (WLAN), Wi-Fi, Bluetooth, or ZigBee, or a combination thereof. The communication method is not limited and may also include short-range wireless communication between the user terminals 210_1, 210_2, and 210_3 as well as a communication method utilizing a communication network that may be included in the network 220 (e.g., a mobile communication network, the wired Internet, the wireless Internet, a broadcast network, or a satellite networks).

The plurality of user terminals 210_1, 210_2, and 210_3 may receive some or all of the data included in the genetic information analysis result report from the information processing system 230 using the genetic information analysis service and the associated application. As another example, the user terminals 210_1, 210_2, and 210_3 may receive some or all of the data included in the genetic information analysis result report from the information processing system 230 using a web browser. The user terminals 210_1, 210_2, 210_3 may output some of the information included in the genetic information analysis result report (e.g., details of the genetic information analysis result) using the user interfaces, a description of which will follow. Upon receiving user input such that a specific menu or a specific graphic object is selected in the user interface, each of the user terminals 210_1, 210_2, and 210_3 may output interactive response information corresponding to the user input. Here, the reactive response information may include details of the genetic information analysis results.

According to an embodiment, upon receiving user input via the user interface, each of the user terminals 210_1, 210_2, and 210_3 may send a data request associated with the user input to the information processing system 230. Subsequently, each of the user terminals 210_1, 210_2, and 210_3 may receive data associated with the user input (e.g., details of the genetic information analysis results) from the information processing system 230 and may output the same via the user interface.

In FIG. 2, a mobile phone terminal 210_1, a tablet terminal 210_2, and a PC terminal 210_3 are shown as examples of the user terminals. However, the present disclosure is not limited thereto, and the user terminals 210_1, 210_2, and 210_3 may be any computing devices capable of performing wired and/or wireless communication and having an application, a web browser, or the like installed therein so as to be executable. For example, the user terminal may include a smartphone, a mobile phone, a navigation device, a computer, a laptop computer, a digital broadcasting terminal, a personal digital assistant (PDA), a portable multimedia player (PMP), or a tablet PC. In addition, although three user terminals 210_1, 210_2, and 210_3 are shown as communicating with the information processing system 230 over the network 220 in FIG. 2, the present disclosure is not limited thereto, and a different number of user terminals may be configured to communicate with the information processing system 230 over the network 220. Although the user terminals and the information processing system are shown as communicating with each other as separate devices in FIG. 2, which is only an embodiment, the genetic information analysis-related configuration and/or function provided by each user terminal and the genetic information analysis-related configuration and/or function provided by the information processing system may be implemented on a single computing device.

Figure 3:
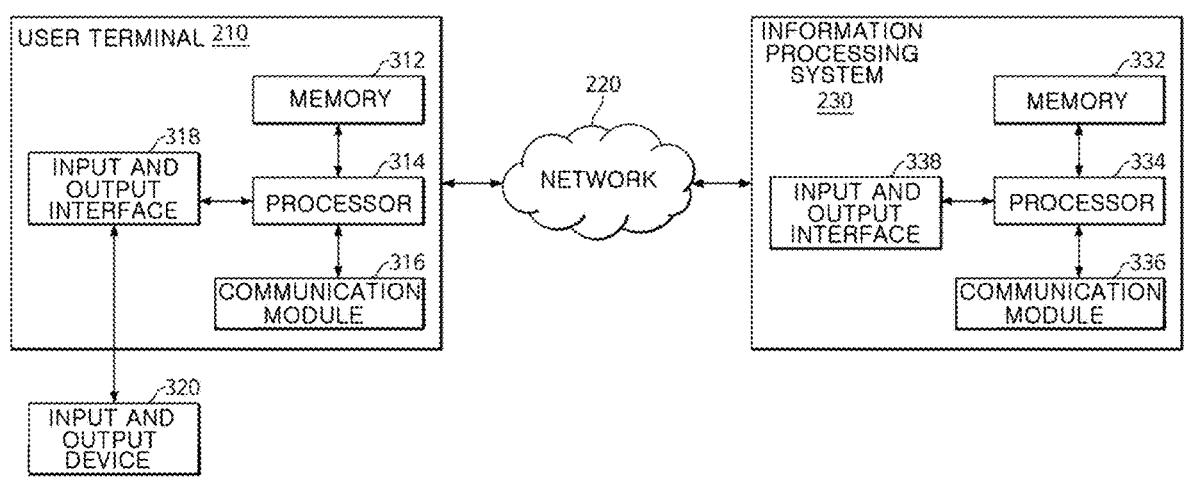
FIG. 3 is a block diagram showing an internal configuration of each of a user terminal according to an embodiment of the present disclosure and the information processing system.

FIG. 3 is a block diagram showing an internal configuration of each of a user terminal 210 according to an embodiment of the present disclosure and the information processing system 230. The user terminal 210 may refer to any computing device capable of executing an application associated with the genetic information analysis service, a web browser configured to provide the genetic information analysis service, and the like, and capable of performing wired or wireless communication, and may include, for example, the mobile phone terminal 210_1, the tablet terminal 210_2, and the PC terminal 210_3 of FIG. 2.

As shown, the user terminal 210 may include a memory 312, a processor 314, a communication module 316, and an input and output interface 318. Similarly, the information processing system 230 may include a memory 332, a processor 334, a communication module 336, and an input and output interface 338. As shown in FIG. 3, the user terminal 210 and the information processing system 230 may be configured to communicate information and/or data over the network 220 using communication modules 316 and 336, respectively. In addition, the input and output device 320 may be configured to input information and/or data to the user terminal 210 and/or to output information and/or data generated from the user terminal 210 via the input and output interface 318.

Each of the memories 312 and 332 may include any non-transitory computer-readable recording medium. According to an embodiment, each of the memories 312 and 332 may include a permanent mass storage device, such as read only memory (ROM), a disk drive, a solid state drive (SSD), or flash memory. As another example, the permanent mass storage device, such as the ROM, the SSD, the flash memory, or the disk drive, may be included in the user terminal 210 or the information processing system 230 as a separate permanent storage device distinct from the memory. In addition, each of the memories 312 and 332 may store an operating system and at least one type of program code (e.g., code for an application associated with the genetic information analysis service installed on and executed by the user terminal 210 or code for a web browser configured to provide the genetic information analysis service).

These software components may be loaded from a computer-readable recording medium separate from the memories 312 and 332. Such a separate computer-readable recording medium may include a recording medium directly connectable to the user terminal 210 and the information processing system 230, for example, a computer-readable recording medium, such as a floppy drive, a disk, a tape, a DVD/CD-ROM drive, or a memory card. As another example, the software components may be loaded into each of the memories 312 and 332 through a communication module rather than the computer-readable recording medium. For example, at least one program may be loaded into each of the memories 312 and 332 based on a computer program that is installed by files provided over the network 220 by a developer or a file distribution system that distributes an application installation file.

Each of the processors 314 and 334 may be configured to process commands of a computer program by performing basic arithmetic, logic, and input and output operations. The commands may be provided to the processors 314 and 334 by the memories 312 and 332 or the communication modules 316 and 336. For example, the processor 314 or 334 may be configured to execute received commands in accordance with program code stored in a recording device such as the memory 312 or 332.

The communication modules 316 and 336 may provide a configuration or function for the user terminal 210 and the information processing system 230 to communicate with each other over the network 220, and may provide a configuration or function for the user terminal 210 and/or the information processing system 230 to communicate with another user terminal or another system (e.g., a separate cloud system). As an example, a request (e.g., a request for details of the genetic information analysis results) or data generated by the processor 314 of the user terminal 210 in accordance with program code stored in a recording device, such as the memory 312, may be transmitted to the information processing system 230 over the network 220 under the control of the communication module 316. Conversely, at least one of a control signal, a command, or data (e.g., details related to the genetic information analysis results) provided under the control of the processor 334 of the information processing system 230 may be received by the user terminal 210 through the communication module 316 of the user terminal 210 via the communication module 336 and the network 220.

The input and output interface 318 may be a means for interfacing with the input and output device 320. As an example, the input device may include a device, such as a camera including an audio sensor and/or an image sensor, a keyboard, a microphone, or a mouse, and the output device may include a device, such as a display, a speaker, or a haptic feedback device. As another example, the input and output interface 318 may be a means for interfacing with a device having an integrated configuration or function for performing input and output, such as a touchscreen. For example, when the processor 314 of the user terminal 210 processes the command of the computer program loaded into the memory 312, a service screen configured using information and/or data provided by the information processing system 230 or another user terminal may be displayed on the display through the input/output interface 318. Although the input and output device 320 is shown as not being included in the user terminal 210 in FIG. 3, the present disclosure is not limited thereto, and the input and output device may be configured as a single device with the user terminal 210. In addition, the input and output interface 338 of the information processing system 230 may be a means for interfacing with a device (not shown) for input or output that may be connected to or include the information processing system 230. Although the input and output interfaces 318 and 338 are shown as separate elements from the processors 314 and 334 in FIG. 3, the present disclosure is not limited thereto, and, the input and output interfaces 318 and 338 may be configured to be included in the processors 314 and 334, respectively.

Each of the user terminal 210 and the information processing system 230 may include more elements than the elements of FIG. 3. However, it is not necessary to clearly show most conventional elements. According to an embodiment, the user terminal 210 may be implemented to include at least a part of the input and output device 320. In addition, the user terminal 210 may further include other elements, such as a transceiver, a global positioning system (GPS) module, a camera, various sensors, and a database. For example, when the user terminal 210 is a smartphone, the user terminal may generally include an element included in the smartphone, and the user terminal 210 may be implemented to further include various elements, such as an accelerometer, a gyro sensor, an image sensor, a proximity sensor, a touch sensor, an illumination sensor, a camera module, various physical buttons, a button using a touch panel, an input and output port, and a vibrator for vibration.

During operation of the program for the application or the web browser providing the genetic information analysis service, the processor 314 may receive text, an image, video, voice, and/or an operation, input or selected through an input device, such as a touchscreen, a keyboard, a camera including an audio sensor and/or an image sensor, a microphone, connected to the input-output interface 318, may store the received text, images, video, voice, and/or operation in the memory 312, or may provide the same to the information processing system 230 via the communication module 316 and network 220.

The processor 314 of the user terminal 210 may be configured to manage, process, and/or store information and/or data received from the input and output device 320, another user terminal, the information processing system 230, and/or a plurality of external systems. Information and/or data processed by the processor 314 may be provided to the information processing system 230 via the communication module 316 and the network 220. The processor 314 of the user terminal 210 may transmit the information and/or the data to the input and output device 320 via the input and output interface 318 so as to be output. For example, the processor 314 may output the received information and/or data to control a display device included in or connected to the user terminal 210 such that the received information and/or data are displayed on a screen of the user terminal 210.

The processor 334 of the information processing system 230 may be configured to manage, process, and/or store information and/or data received from a plurality of user terminals 210 and/or a plurality of external systems. The information and/or the data processed by the processor 334 may be provided to the user terminal 210 via the communication module 336 and the network 220.

Although not shown in the figure, the information processing system 230 may include at least one database configured to store a genetic information analysis result report including genome analysis information. According to an embodiment, the information processing system 230 may store a specimen-specific genetic information analysis result report, and may store identification information of at least one specimen included in each project. Accordingly, one project may include a genetic information analysis result report for at least one specimen. Here, the genetic information analysis result report may include the location of each mutation, the type of each mutation, information about a patient from whom the sample was collected, statistical information about the analysis results, comment information about the analysis results, a list of drivers associated with a specific disease, information about a gene in which the mutations occurred, information related to tumor mutational burden (TMB), and information related to mutation signature. Details included in the genetic information analysis result report may be output to at least one region included in the user interface.

In addition, the database may store user information, including user's ID, password, full name, date of birth, mobile phone number, and email address. In addition, the database may store information of multiple users (i.e., member information) participating in each project. According to an embodiment, the database may store a list of major mutations associated with each disease. For example, a list of first major mutations associated with a first disease may be stored in the database, and a list of second major mutations associated with a second disease may be stored in the database. Here, the list of major mutations may include mutations known to the field to be important in the associated disease. In addition, the database may store a list of genes associated with each of one or more diseases. Here, the list of genes may include labels for mutated genes that are known to be important in the disease.

Figure 4:
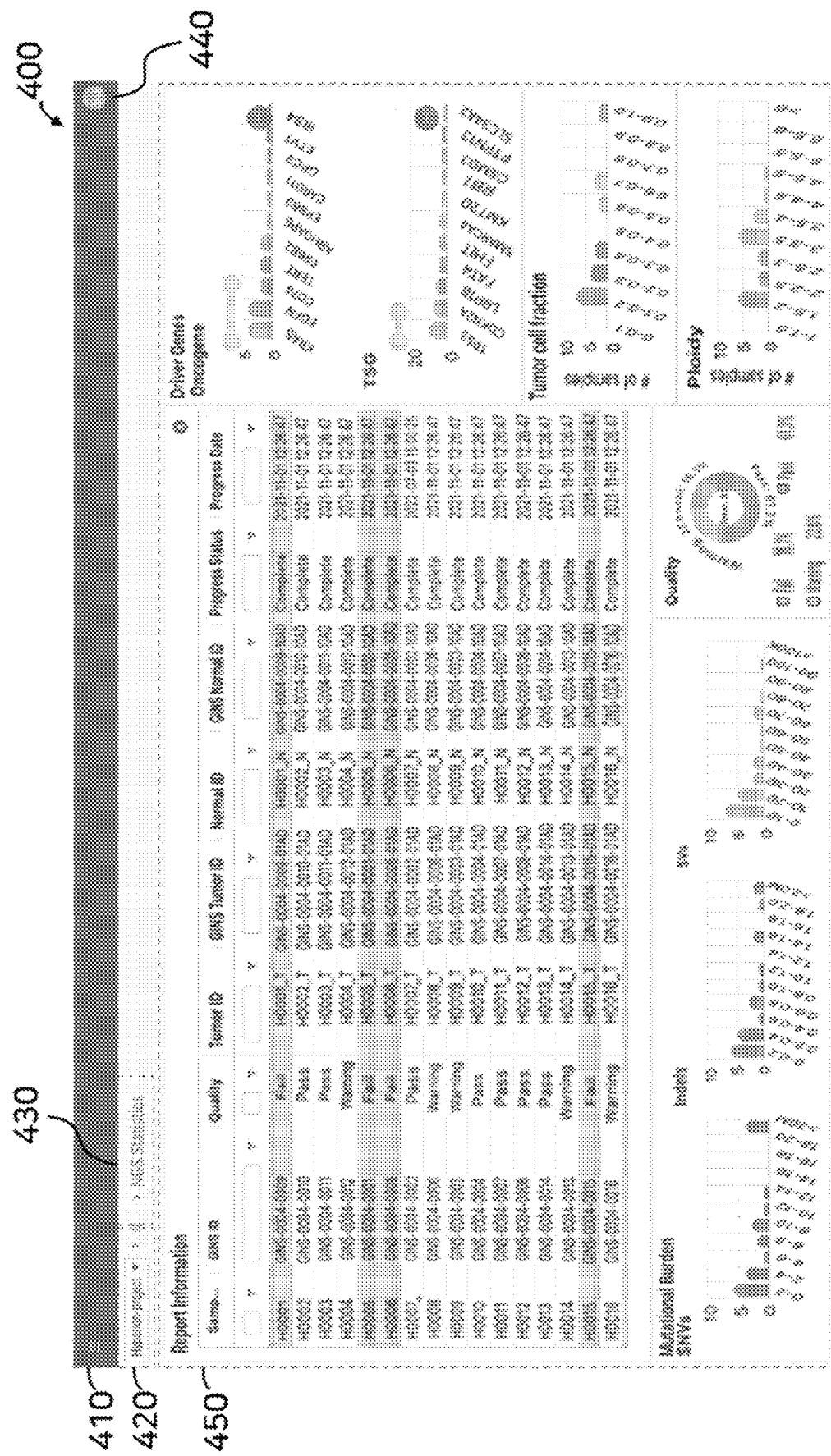
FIG. 4 is a view illustrating an initial screen output upon successful login authentication according to an embodiment of the present disclosure.

FIG. 4 is a view illustrating an initial screen 400 output upon successful login authentication according to an embodiment of the present disclosure. As illustrated in FIG. 4, when the user terminal accesses the information processing system and successfully logs in, the initial screen 400 as shown in FIG. 4 may be output to the user terminal.

The initial screen 400 may be configured as a layout having a plurality of partitioned regions. According to an embodiment, the initial screen 400 may be constituted by a first region 410 including menu buttons, a second region 420 including a project selection menu, a third region 430 indicating the location of the current menu, a fourth region 440 displaying logged-in user information, and a fifth region 450 outputting statistical information about analysis results of each specimen included in the project and specimen-specific brief information.

When a menu included in the first region 410 is selected, a first submenu for checking statistical information and a second submenu for checking information about the analysis results may be output. In addition, when a menu included in the first region 410 is selected, various submenus may be output in addition to the first submenu and the second submenu. The user may obtain relevant information by selecting a submenu.

The second region 420 may include a project selection menu used to output a list of projects in which the successfully logged-in user is participating. When the project selection menu is selected, a list of projects assigned to the user may be output to the user terminal.

Information about the menu that is currently being used may be output to the third region 430. In FIG. 4, the menu related to next-generation sequencing (NGS) statistics is illustrated as being used.

User information including the user's login ID may be output to the fourth region 440.

Brief information and statistical information about each specimen included in the project may be output to the fifth region 450. The statistical information output to the fifth region 450 will be described in detail with reference to FIG. 5.

The user may select another project using the project selection menu included in the second region 420. When a second project different from the first project output to the initial screen 400 is selected through the project selection menu, statistical information and brief information about specimen-specific analysis results included in the second project may be output to the fifth region 450.

Figure 5:
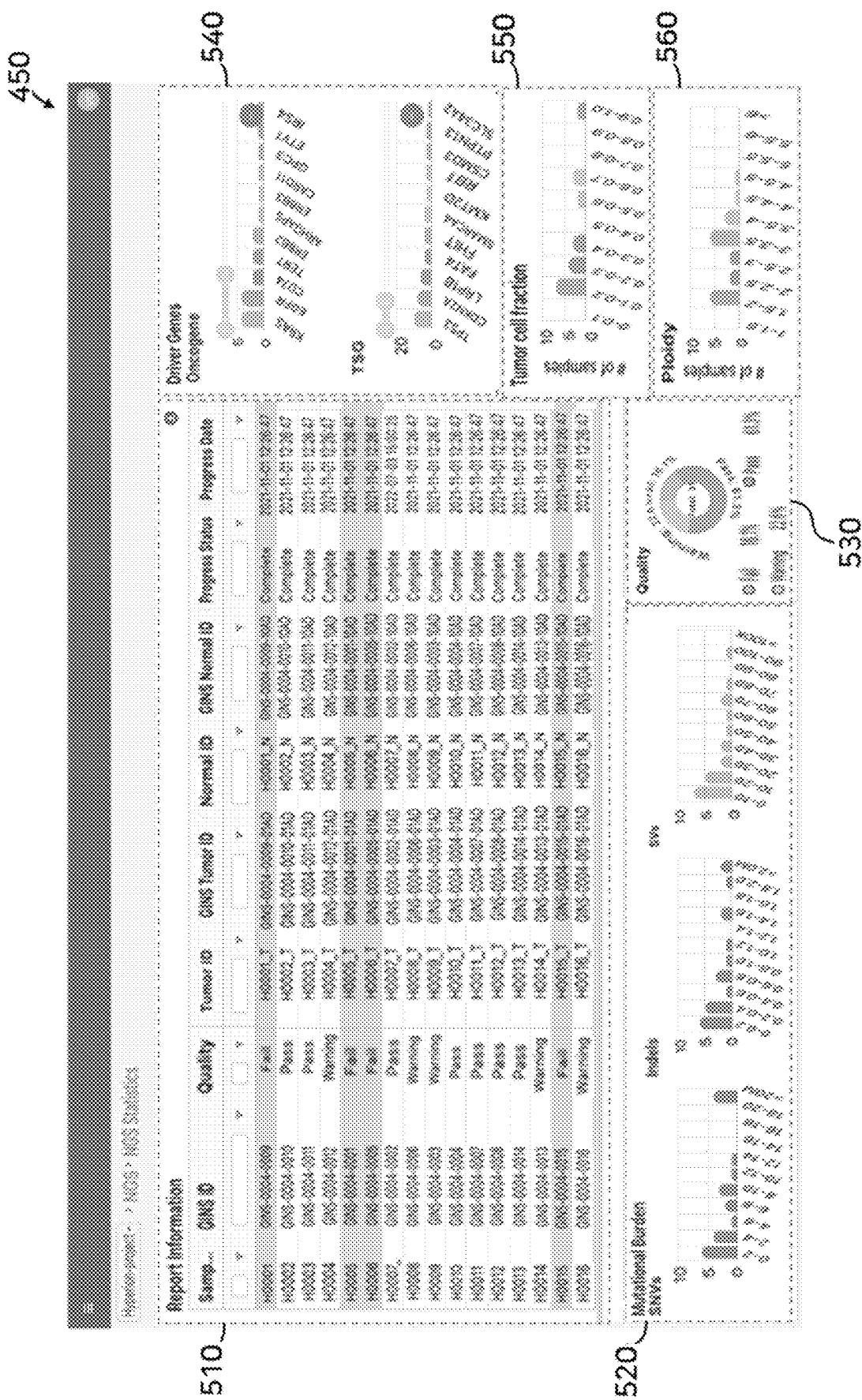
FIG. 5 is a view illustrating a layout for a fifth region of FIG. 4 according to the embodiment of the present disclosure.

FIG. 5 is a view illustrating a layout for the fifth region 450 of FIG. 4 according to the embodiment of the present disclosure. Referring to FIG. 5, the fifth region 450 included in the initial screen 400 may be configured as a layout including a plurality of subregions 510 to 560.

Brief information about analysis results for each specimen may be output to the first subregion 510. For example, the brief information about analysis results may include a sample ID for the specimen, the quality of the analysis results, tumor identification information, and an analysis completion date. For example, good quality of the analysis results may be labeled as "pass", and poor quality of the analysis results may be labeled as "fail" or "warning" depending on the quality.

Statistical information of tumor mutational burden may be output to the second subregion 520. As illustrated in FIG. 5, statistical information of tumor mutational burden for each of a single nucleotide variation, an indel (insertion & deletion), and structural variants (SVs) may be output. Here, the statistical information may be calculated based on all specimens included in the project. As illustrated in FIG. 5, a certain number of regions corresponding to tumor mutational burden may be partitioned, and the number of detections of tumor mutational burden for each region may be output to the second subregion 520 in the form of a graph.

Statistical information about sequencing quality of for the project may be output to the third subregion 530. For example, statistics on sequencing quality of each specimen included in the project may be calculated, and the calculated statistics may be output to the third subregion 530 in the form of a graph.

Statistical information of mutations for driver genes associated with a specific disease (e.g., cancer) may be output to the fourth subregion 540. The statistical information output to the fourth subregion 540 may be generated based on the results of analysis of mutations found in each specimen included in the project. The number of detections of each mutation associated with an oncogene is output to the upper part of the fourth subregion 540 in the form of a bar graph, and the number of detections of each mutation associated with a tumor suppressor gene is output to the lower part of the fourth subregion 540 in the form of a bar graph.

The ratio of tumor cells to normal cells may be output to the fifth subregion 550 in the form of a graph. Here, the ratio of tumor cells to normal cells may be calculated for each predetermined interval, and the calculated ratio may be output in each interval in the form of a graph.

The degree of ploidy may be output to the sixth subregion 560 in the form of a graph. According to an embodiment, the degree of ploidy of each specimen included in the project may be calculated for each predetermined interval, and the calculated degree of ploidy may be output in each interval in the form of a graph.

Meanwhile, when any one is selected from specimens included in the first subregion 510 of FIG. 5, a user interface including a first browser and a second browser capable of checking analysis results for the selected specimen in detail may be output.

Figure 6:
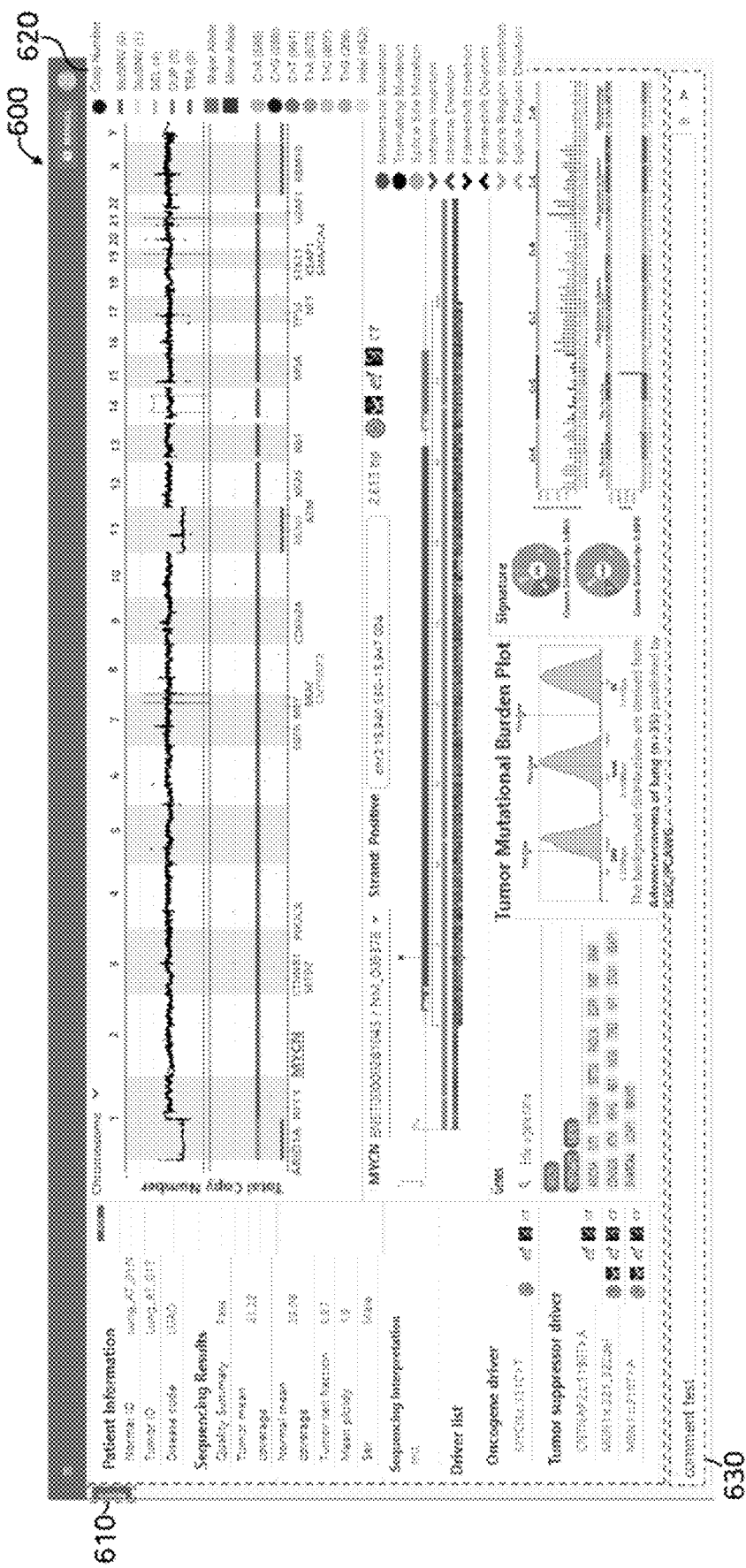
FIG. 6 is a view illustrating a user interface including a first browser and a second browser according to an embodiment of the present disclosure.

FIG. 6 is a view illustrating a user interface 600 including a first browser and a second browser according to an embodiment of the present disclosure. As illustrated in FIG. 6, the user interface 600 may be configured as a layout having a plurality of partitioned regions 610, 620, and 630.

A menu for selecting projects and specimens may be output to the first region 610 included in the user interface 600. When the menu is selected, a list of projects and a list of specimens may be output through the user interface 600.

Details of specimen analysis results may be output to the second region 620 included in the user interface 600. The second region 620 may include a plurality of browsers and a plurality of subregions. A layout of the second region 620 will be described below with reference to FIG. 7.

The third region 630 included in the user interface 600 may include a comment field for exchanging comments with other users participating in the project. The information processing system may store at least one of email addresses, contacts, and terminal IP addresses of users participating in each project. When a specific user enters a comment in the comment field of the third region 630, the comment may be provided to other users participating in the project. For example, when a user enters a comment in the comment field, the information processing system may obtain the comment entered by the user, may identify a project associated with the specimen output through the user interface, and may provide the user's comment to at least one other user participating in the identified project. At this time, the information processing system may email the comment to the other user or send the comment to a user terminal held by the other user.

Figure 7:
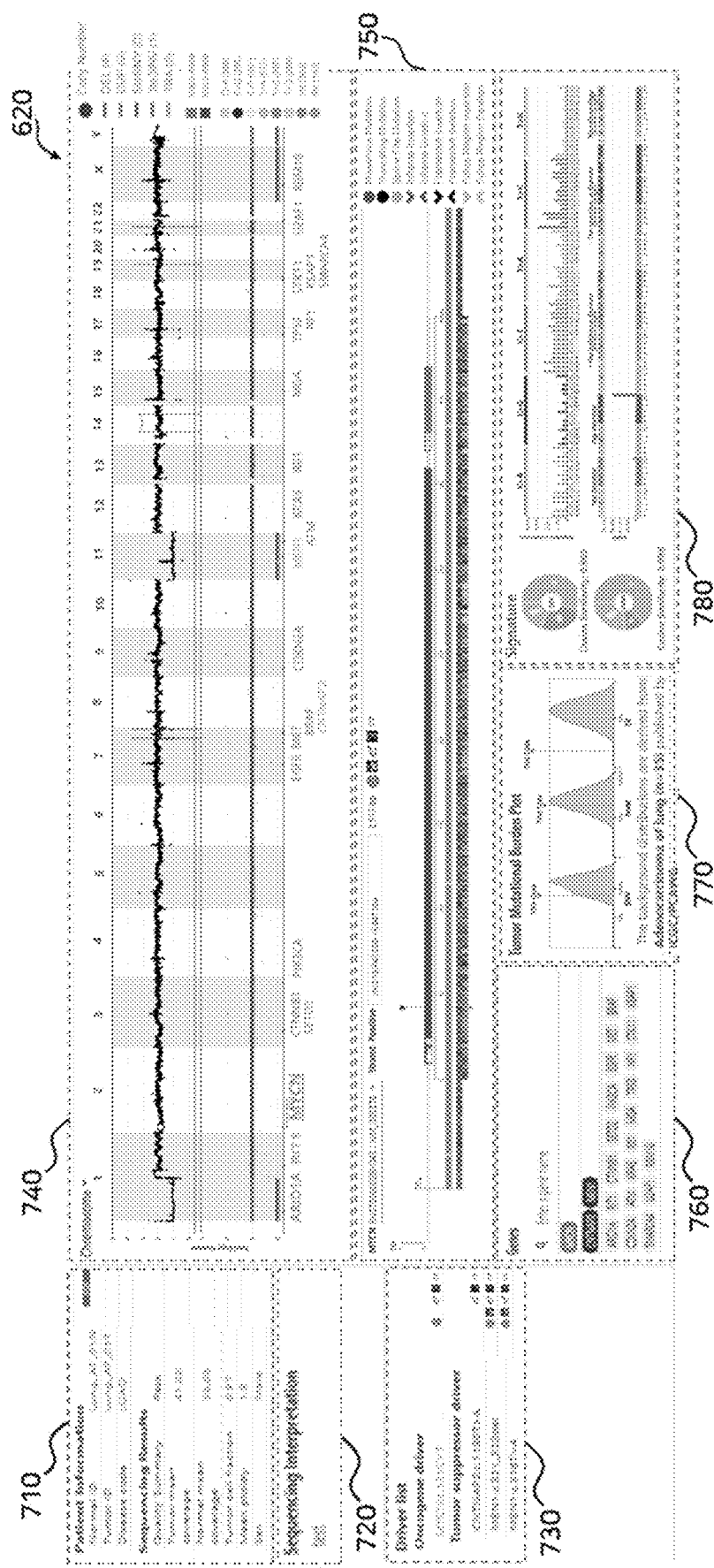
FIG. 7 is a view illustrating a layout for a second region of FIG. 6 according to the embodiment of the present disclosure.

FIG. 7 is a view illustrating the layout for the second region 620 of FIG. 6 according to the embodiment of the present disclosure. As illustrated in FIG. 7, the second region 620, to which analytical results for the specimen are output, may be configured as a layout including a plurality of subregions 710 to 780.

Patient information and statistical information about the sequencing results may be output to, or displayed in, the first subregion 710. As illustrated in FIG. 7, patient information, including disease-related codes and disease identification information (e.g., cancer identification information), and statistical information about the sequencing results for the specimen may be output to the first subregion 710.

Specimen interpretation information may be output to the second subregion 720. The specimen interpretation information may be comments provided by a human expert analyst. That is, the expert analyst may interpret the sequencing results for the specimen, may pre-enter and store comments about the sequencing results in the information processing system, and when the comments about the sequencing results are stored, the comments made by the expert analyst may be output to the second subregion 720. The specimen interpretation information may include comments automatically generated by a computer program or an artificial intelligence model.

A list of drivers including a list of genes that are associated with a specific disease (e.g., cancer) and are associated with mutations found in the specimen may be output to the third subregion 730. Here, the list of drivers may include a list of mutated genes associated with a specific disease and found in the specimen and information about the mutations. In FIG. 7, the list of drivers is illustrated as a disease associated with cancer. The list of drivers may include a list of oncogene drivers and a list of tumor suppressor drivers. The label of a gene with an oncogene mutation, among the mutations found in the specimen, may be included in the list of oncogene drivers and may be output to the third subregion 730. In addition, the label of a gene mutated to limit or lose a tumor suppressor function, among the mutations found in the specimen, may be included in the list of tumor suppressor drivers and may be output to third subregion 730.

A first browser configured to allow the user to browse the entire base sequence for variants found in the specimen may be output to a fourth subregion 740. In some embodiments, the first browser may provide a view of variants found across the whole genome. The user may enlarge or zoom in on a specific region in the entire base sequence using the first browser, and may select only a region corresponding to at least one chromosome of the genome. In addition, the user may perform various search tasks on the variants found in the specimen using the first browser. When user input is received via the first browser or another region of the user interface 600, reactive response information based on the genome analysis information may be output to the fourth subregion 740 in response to this user input. The reactive response information may include various details about the genetic information analysis results of the specimen. Various functions provided by the first browser will be described below in detail with reference to FIGS. 9 to 15.

A second browser used to search sequence information and other details about the variants obtained by analysis of the specimen may be output to the fifth subregion 750. In some embodiments, the second browser may allow the user to search sequence information obtained as the result of genome analysis navigable at, for example, the gene level and to identify missense mutations and silent mutations. The user may enlarge an amino acid information region and may identify the difference between reference amino acid sequence and amino acid sequence with alterations caused by, for example, genetic variants in the DNA base sequence using the second browser. In addition, the user may perform various search tasks related to genetic information using the second browser.

When user input is received via the second browser or another region of the user interface 600, reactive response information based on the genome analysis information may be output to the fifth subregion 750 in response to the user input. The reactive response information can include genetic information about mutations. Here, the genetic information may include exon associated with the mutated gene, a transcribed and translated amino acid sequence from the base sequence, an untranslated region from the base sequence, and domain information. Various functions provided by the second browser will be described below in detail with reference to FIGS. 16 to 19.

A list of genes associated with a specific disease may be output to the sixth subregion 760. Here, the list of genes may include the label of at least one gene in which a major mutation associated with a specific disease occurs. According to an embodiment, a list of genes associated with a specific disease may be pre-stored in the information processing system, and the information processing system may include the list of genes in the genome analysis information for the specimen. According to an embodiment, a specific disease may be identified based on a disease code included in patient information, and the information processing system may extract a list of genes associated with the identified specific disease from a database and may include the extracted list of genes in the genome analysis information. In the present disclosure, the specific disease is illustrated as cancer.

Upon comparing the list of drivers included in the third subregion 730 to the list of genes included in the sixth subregion 760, the list of genes output to the sixth subregion 760 may include gene labels associated with mutations found in the specimen and gene labels not found in the specimen, whereas the list of drivers output to the third subregion 730 may include only gene labels associated with mutations found in the specimen. Here, the gene labels may be gene names or other gene identifiers.

Information related to tumor mutational burden of the specimen may be output to the seventh subregion 770. Statistical information of tumor mutational burden for each of a single nucleotide variation, an indel, and structural variants (SVs) for the specimen may be calculated and output to the seventh subregion 770 in the form of a graph. Information associated with tumor mutational burden output to the seventh subregion 770 will be described below in detail with reference to FIG. 26.

Information associated with a mutational signature for the specimen may be output to the eighth subregion 780. The information associated with the mutational signature may include single base substitution (hereinafter referred to as "SBS") signature information and indel signature information. The mutational signature information output to the eighth subregion 780 will be described below in detail with reference to FIG. 27.

Figure 8:
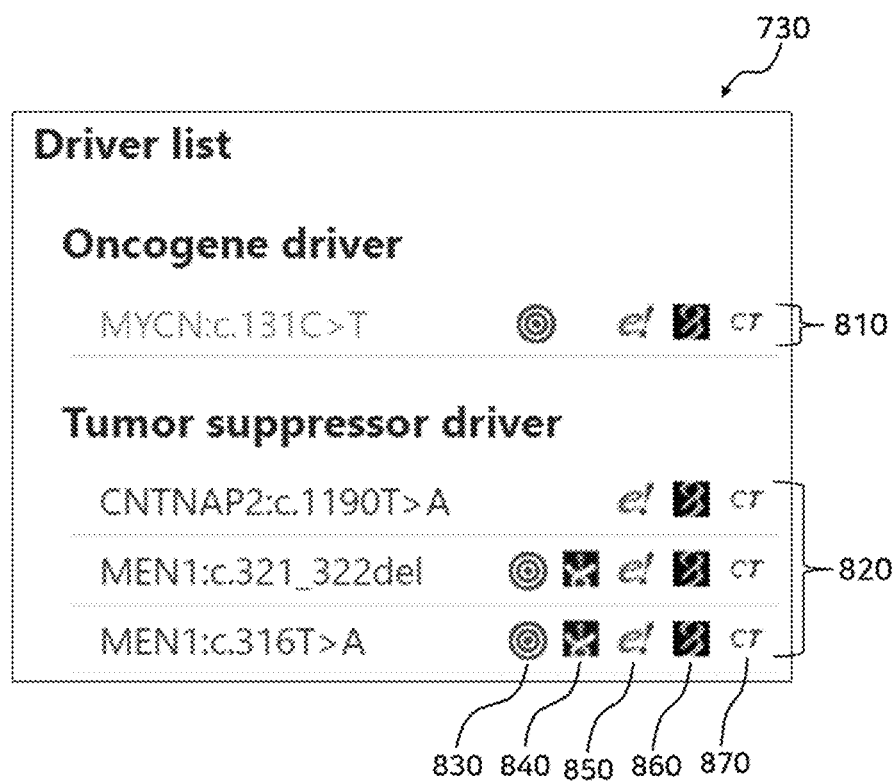
FIG. 8 is an enlarged view of a third subregion of FIG. 7.

FIG. 8 is an enlarged view of the third subregion 730 of FIG. 7. A list of drivers including a list of genes associated with a specific disease (e.g., cancer) and associated with mutations found in the specimen may be output to the third subregion 730. Here, the list of genes may include at least one gene label.

As illustrated in FIG. 8, when a disease to be analyzed is a disease associated with cancer, the list of drivers may include a list of oncogene drivers 810 and a list of tumor suppressor drivers 820. In FIG. 8, it is illustrated that the list of oncogene drivers 810 includes an "MYON" gene label and mutation information in which a base "C" is substituted by a base "T" in a gene having the "MYCN" gene label and the list of tumor suppressor drivers 820 includes a "CNT-NAP2" gene label and a "MEN1" gene label and further including mutation information that has occurred in each of genes having the "CNTNAP2" gene label and the "MEN1" gene label. In addition, the gene labels and the mutation information included in the list of oncogene drivers 810 may be visualized using a first graphic element (e.g., a first color) and may be output to the third subregion 730. The gene labels and the mutation information included in the list of tumor suppressor drivers 820 may be visualized using a second graphic element (e.g., a second color) and may be output to the third subregion 730. In FIG. 8, the gene labels and the mutation information are illustrated as being separated by a delimiter (:).

In one embodiment, the drivers can be categorized and visually differentiated based on their variant types. For instance, the drivers can be organized into distinct groups, such as substitution, copy number alteration, and structural variation. Additionally, somatic mutations and germline mutations can be presented separately to provide clearer differentiation.

At least one link icon 830 to 870, adjacent to the label of each gene, may be output to the third subregion 730 to enable an external database to be accessed.

Each of the link icons 830 to 870 is a means configured to enable access to an external database that provides at least one of a detailed description of each mutation, comment information, a treatment method, and effects of the treatment method, and the link icons 830 to 870 may include link addresses to different external databases.

The first link icon 830 may include a link to access a first external database (e.g., "OncoKB" database) that provides at least one of a detailed description of a mutation, comment information, a treatment method, and effects of the treatment method. When the first link icon 830 is clicked or touched, the user interface may access the first external database to obtain at least one of the detailed description of the mutation, the comment information, the treatment method, or the effects of the treatment method, and may output a web page including the obtained information. When information associated with the gene label output to the third subregion 730 is included in the first external database, the first link icon 830 may be activated and output to the third subregion 730.

Similarly, the second link icon 840 may include a link to access a second external database (e.g., "CIVIC" database) that provides at least one of a detailed description of a mutation, comment information, a treatment method, or effects of the treatment method. When the second link icon 840 is clicked or touched, the user interface may access the second external database to obtain at least one of the detailed description of the mutation, the comment information, the treatment method, or the effects of the treatment method, and may output a web page including the obtained information. When information associated with the gene label output to the third subregion 730 is included in the second external database, the second link icon 840 may be activated and output to the third subregion 730.

In addition, the third link icon 850 may include a link to access a third external database (e.g., "Ensembl" database) that provides at least one of a detailed description of a mutation, comment information, a treatment method, or effects of the treatment method. When information associated with the gene label output to the third subregion 730 is included in the third external database, the third link icon 850 may be activated and output to the third subregion 730. Similarly, the fourth link icon 860 may include a link to access a fourth external database (e.g. "UCSC Genome Institute" database) that provides at least one of a detailed description of a mutation, comment information, a treatment method, or effects of the treatment method, and the fifth link icon 870 may include a link to access a fifth external database (e.g. "ClinicalTrials.gov" database) that provides at least one of a detailed description of a mutation, comment information, a treatment method, or effects of the treatment method. When information associated with the gene label is included in the fourth external database, the fourth link icon 860 may be activated and output to the third subregion 730. When information associated with the gene label is included in the fifth external database, the fifth link icon 870 may be activated and output to the third subregion 730.

Figure 9:
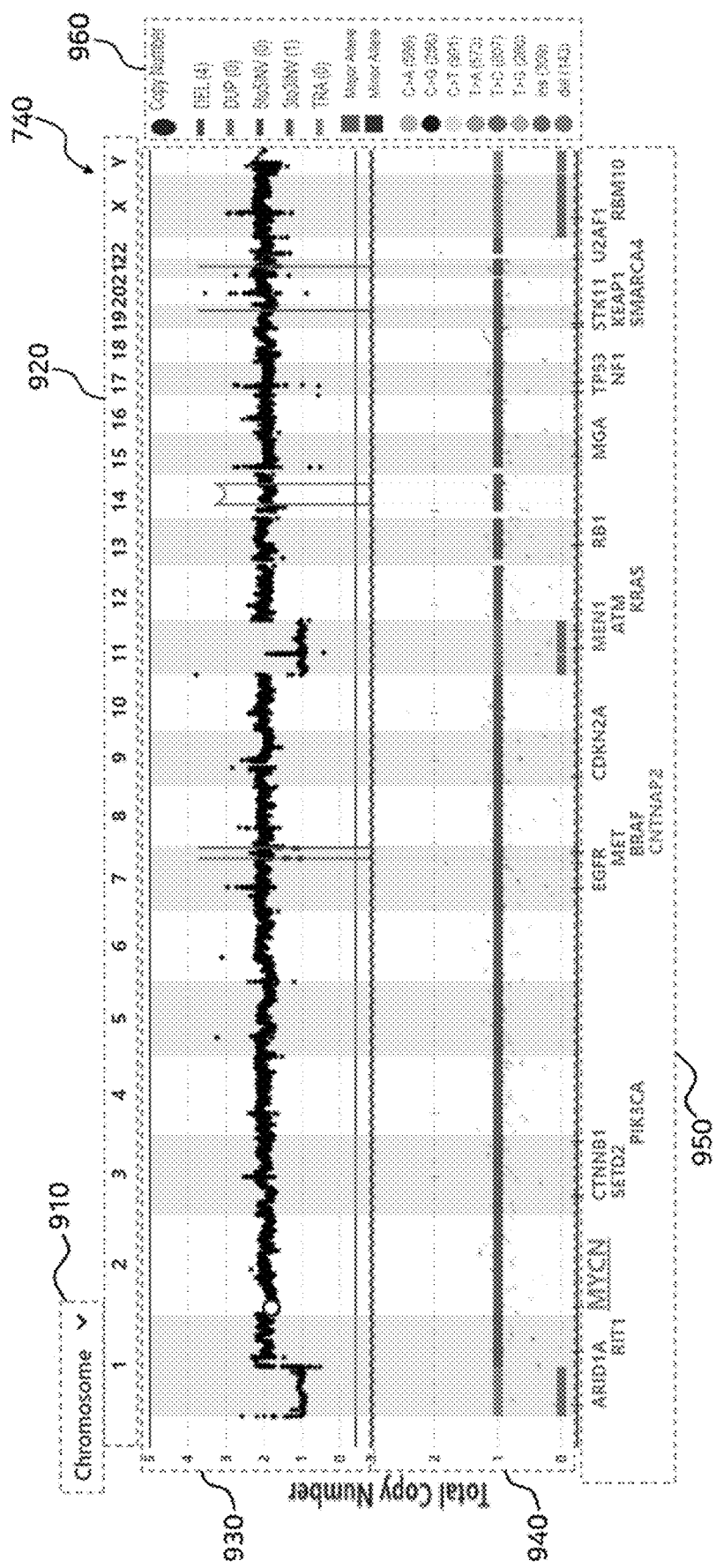
FIG. 9 is an enlarged view of a fourth subregion of FIG. 7 where the first browser is provided.

FIG. 9 is an enlarged view of the fourth subregion 740 of FIG. 7 where the first browser is provided. As illustrated in FIG. 9, the first browser may be configured as a layout including a menu region 910 for selecting at least one chromosome, a chromosome display region 920 in which chromosome identification information is displayed, a first information output region 930 to which structural variation and copy number information is output, a second information output region 940 to which a point mutation and sequence-delimited (allelic) copy number information (e.g. copy number of a chromosome from a paternal line and copy number of a chromosome from a maternal line) is output, a gene label output region 950 to which the label of a gene in which variants have been found or not found is output, and a filtering region 960 utilized to filter the type of variants to be visibly output to the first browser.

The information output to each of the menu region 910, the first information output region 930, the second information output region 940, and the gene label output region 950 may be controlled through the first browser.

When a chromosome menu in the menu region 910 is selected, a list of chromosomes included in the base sequence may be output. One or more chromosomes may be selected from the list of chromosomes, and the first browser may be controlled such that only information associated with the selected chromosomes is selected and output to the first information output region 930, the second information output region 940, and the gene label output region 950.

Identification information for each chromosome may be output to the chromosome display region 920. In FIG. 9, all chromosomes are illustrated as being output.

A pattern plotting the copy number of each region/location of a genome as black dots may be output to the first information output region 930 through the first browser. Additionally, point mutations and structural variants may be visualized and output to the first information output region 930 through the first browser. According to an embodiment, a graphic object associated with structural variants found in the specimen may be visualized and output to the first information output region 930. At this time, at least one of the shape and color of the graphic object may be determined based on the type of a target structural variation to be visualized, and the size (e.g., width) of the graphic object may be determined based on the region (location range) of the target structural variation and may be visualized in the first information output region 930.

In FIG. 9, it is illustrated that five structural variants are visualized and output to the first information output region 930 and different colors and/or shapes are visualized depending on the type of the structural variants.

Information about the number of copies for each allele may be output to the second information output region 940. In FIG. 9, it is illustrated that the copy number of one allele (e.g., the copy number of the allele received from the maternal line) is visualized using a first graphic element (e.g., a first color) and the copy number of another allele (e.g., the copy number of the allele received from the paternal line) is visualized using a second graphic element (e.g., a second color) in the second information output area 940.

In addition, a point mutation found in the base sequence may be visualized and output to the second information output region 940. Based on the type of the variant, the graphic element that visualizes the variant may be determined. For example, a "C>A" variant with a base "C" substituted by "A" may be visualized using a third graphic element, a "C>G" variant with a base "C" substituted by "G" may be visualized using a fourth graphic element, and a "C>T" variant with a base "C" substituted by "T" may be visualized using a fifth graphic element.

Each of genes associated with major mutations associated with a specific disease may be output to the gene label output region 950 in association with the location thereof. In addition, the gene associated with the mutation found in the specimen, among the genes associated with the major mutations output to the gene label output region 950, may be visualized using a separate graphic element. According to an embodiment, the gene found in the specimen and included in the list of oncogene drivers, among the genes associated with the major mutations, may be visualized in the gene label output region 950 using a sixth graphic element. In addition, the gene found in the specimen and included in the list of tumor suppressor drivers, among the genes associated with the major mutations, may be visualized in the gene label output region 950 using a seventh graphic element. Furthermore, the gene associated with a mutation not found in the specimen, among the genes associated with the major mutations, may be visualized in the gene label output region 950 using an eighth graphical element. In FIG. 9, it is illustrated that the "MYON" gene included in the list of oncogene drivers is visualized using a third color as the sixth graphical element, the "CNTNAP2" and "MEN1" genes included in the list of tumor suppressor drivers are visualized using a fourth color as the seventh graphical element, and the genes associated with the major mutations not found in the specimen, such as "ARID1A" and "RIT1", are visualized using a fifth color as the eighth graphical element.

The filtering region 960 may include first filter objects capable of filtering the structural variants output to the first information output region 930 and second filter objects capable of filtering the variants output to the second information output region 940.

The first filter objects included in the filtering region 960 may include objects associated with structural variants. Referring to FIG. 9, the first filter objects may include a "DEL" object representing a structural variant associated with deletion, a "DUP" object representing a structural variant associated with duplication, a "5to5INV" object and a "3to3INV" object representing a structural variant associated with inversion, and a "TRA" object representing a structural variant associated with translocation. The number in parentheses next to each object may be the number of mutations of that structure found in the specimen.

Information about a structural variant of the type associated with the filter object selected by the user (i.e., a graphic object associated with the structural variant) may be selected from among the first filter objects, and may be visibly output to the first information output region 930. In addition, information about a structural variant of the type associated with a filter object not selected by the user (i.e., a graphic object associated with the structural variant) from among the first filter objects may be removed from the first information output region 930 or may not be visualized therein. The user may select information about the structural variant to be checked and may output the same to the first information output region 930 by selecting an object included in the first filter objects.

The second filter objects included in the filtering region 960 may include objects associated with variants other than structural variants. Referring to FIG. 9, the second filter objects may include a "major allele" object representing the number of copies of the allele received from one of the maternal and paternal lines and a "minor allele" object representing the number of copies of the allele received from the other of the maternal and paternal lines. Here, when the "major allele" object represents the number of copies of the allele received from the maternal line, the "minor allele" object may represent the number of copies of the allele received from the paternal line. Conversely, when the "major allele" object represents the number of copies of the allele received from the paternal line, the "minor allele" object may represent the number of copies of the allele received from the maternal line.

In addition, the second filter objects may include a plurality of objects associated with the point mutation. In FIG. 9, the objects associated with the point mutation are illustrated as a "C>A" object, a "C>G" object, a "C>T" object, a "T>A" object, a "T>C" object, and a "T>G" object. Additionally, the second filter objects may include an "ins" object associated with insertion and a "del" object associated with base deletion. The number in parentheses next to each object may be the number of variants detected in the base sequence.

The copy number and/or variant associated with the object selected from among the second filter objects may be selected and visibly output to the second information output region 940, and the copy number and/or variant associated with the object not selected from among the second filter objects may be removed from the second information output area 940 or may not be visualized therein. The user may select the paternal/maternal copy number and/or variant to be checked and may output the same to the second information output region 940 by selecting an object included in the second filter objects.

Figure 10:
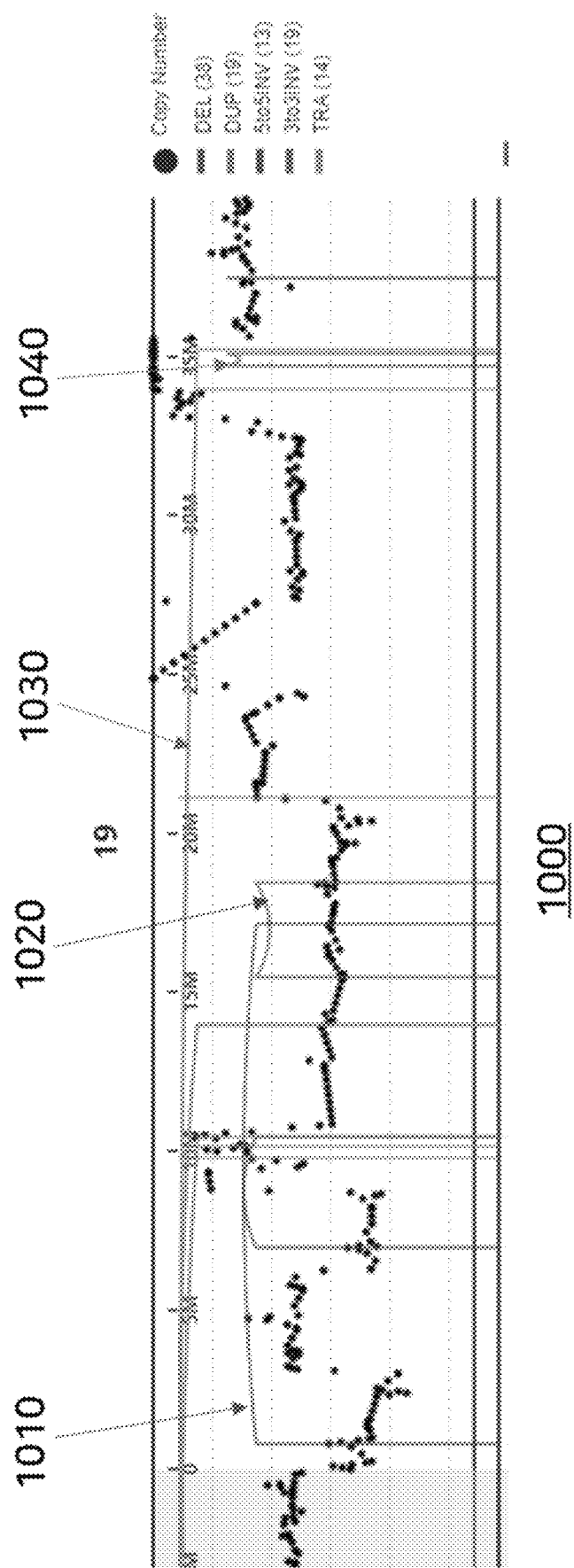
FIG. 10 is a view showing another example of a first information output region including structural variants visualized through different graphic objects.

FIG. 10 is a view showing another example of a first information output region 1000 including structural variants visualized through different graphic objects. As illustrated in FIG. 10, graphic objects associated with the type of structural variants may be determined by the first browser, and the graphic objects may be visualized in the first information output region 1000.

A first type of structural variant 1010 associated with n bases (where n is a natural number) being inversed may be visualized in a first information output region 1000 using a first graphic object. In addition, a second type of structural variant 1020 associated with m bases (where m is a natural number) being inversed may be visualized in the first information output region 1000 using a second graphic object. A third type of structural variant 1030 associated with bases being translocated may be visualized in the first information output region 1000 using a third graphic object. In addition, a fourth type of structural variant 1040 associated with bases being deleted may be visualized in the first information output region 1000 using a fourth graphic object.

As illustrated in FIG. 10, when the structural variants 1010 and 1040 are of different types, the structural variants 1010 and 1040 may be visualized using different graphic objects. For example, different types of structural variants 1010 to 1040 may be visualized using graphic objects having different colors and/or shapes.

Meanwhile, the graphic objects related to the structural variants may be dense and output to the first information output region. For example, when a plurality of structural variants is found in a specific region of the base sequence, the graphic objects associated with the structural variants may be closely located in that region. In this case, the graphic objects associated with the respective structural variants may be overlapping, whereby user readability may be reduced. For this situation, the density of the graphic objects associated with the structural variants is calculated, and when the calculated density exceeds a predetermined threshold, various graphic processing operations may be performed to improve readability. For example, the density of the graphic objects may be calculated based on the number of graphic objects located within a threshold distance. In this case, when more than a threshold number of graphic objects associated with the structural variants are located within the threshold distance, various graphic processing operations may be performed to improve readability. As another example, the density of the graphic objects may be calculated based on the area in which the graphic objects are visualized within a predetermined unit area. In this case, when the calculated density of the graphic objects is equal to or greater than a threshold, various graphic processing operations may be performed to improve readability. In addition, the density of the graphic objects may be calculated using various methods.

Figure 11:
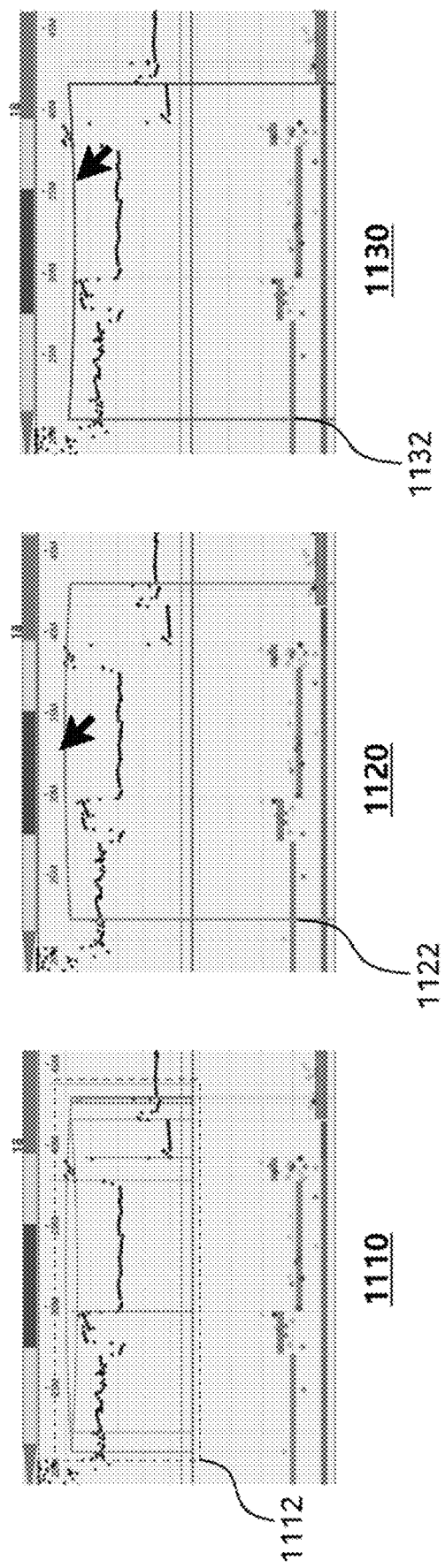
FIG. 11 is a view showing an example of graphic object processing when graphic objects associated with structural variants are dense.

FIG. 11 is a view showing an example of graphic object processing when graphic objects associated with structural variants are dense. As illustrated in a first screen 1110 of FIG. 11, when the graphic objects associated with the structural variants are densely located within a threshold distance, a region 1112 including the threshold distance may be determined to be a dense region 1112 in which the graphic objects are dense. For example, a dense area 1112 having a predetermined distance from the threshold distance as a horizontal width may be determined. According to an embodiment, a determination may be made as to whether more than a threshold number of graphic objects are located within the threshold distance, and when more than a threshold number of graphic objects are located within the threshold distance, the region including the threshold distance may be determined to be a dense region. According to some embodiments, the density of the graphic objects may be calculated based on the area in which at least one graphic object is visualized within a predetermined unit area, and when the calculated density of the graphic objects is equal to or greater than a threshold value, a region including the graphic object may be determined to be a dense region.

In the state in which more than a threshold number of graphic objects are located in the dense region 1112 or the density of the dense region 1112 is equal to or greater than a threshold, a pointer may be located on a first graphic object 1122, among a plurality of graphic objects, as shown in a second screen 1120. In this case, the first browser may be controlled such that that the first graphic object 1122 on which the pointer is located is highlighted. Additionally or alternatively, the first browser may be controlled such that, among the graphic objects included in the dense region 1112, objects other than the first graphic object 1122 on which the pointer is located are removed or blurred. In the second screen 1120 of FIG. 11, it is illustrated that the line of the graphic object 1122 where the pointer is located is thickened and the other objects are blurred.

When the pointer moves from the first object 1122 to a second object 1132, the first browser may be controlled such that the line of the second graphic object 1132 on which the pointer is located is thickened for emphasis and objects other than the second graphic object 1122 are removed or blurred.

Figure 12:
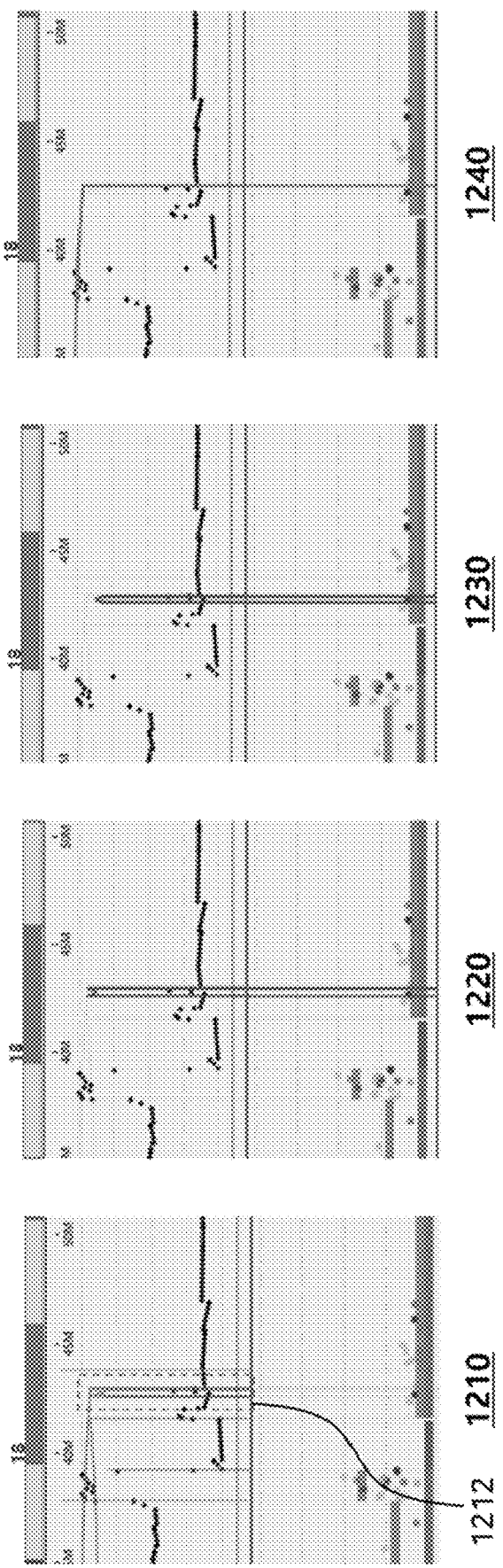
FIG. 12 is a view showing another example of graphic object processing when graphic objects associated with structural variants are dense.

FIG. 12 is a view showing another example of graphic object processing when graphic objects associated with structural variants are dense. As illustrated in a first screen 1210 of FIG. 12, when more than a threshold number of graphic objects associated with the structural variants are densely located within a threshold distance, a region 1212 including the threshold distance may be determined to be a dense region 1212 in which the graphic objects are dense. According to some embodiments, the density of the graphic objects may be calculated based on the area in which at least one graphic object is visualized within a predetermined unit area, and when the calculated density of the graphic objects is equal to or greater than a threshold value, a region including the graphic object may be determined to be a dense region.

In response to determination of the dense region 1212, the first browser may be controlled such that a plurality of graphic objects located in the dense region 1212 is highlighted while being rotated at regular time intervals. For example, the first browser may be controlled such that the first graphic object, the second graphic object, and the third graphic object included in the dense region 1212 are highlighted for visualization while being rotated. At this time, the line of the highlighted graphic object may be thickened, and graphic objects other than the highlighted graphic object may be blurred or removed. As illustrated in FIG. 12, the first browser may be controlled such that a second screen 1220 in which the first graphic object is highlighted, a third screen 1230 in which the second graphic object is highlighted, and a fourth screen 1240 in which the third graphic object is highlighted are rotated in that order.

FIG. 13 is a view showing a further example of graphic object processing when graphic objects associated with structural variants are dense. As illustrated in a first screen 1310 of FIG. 13, when more than a threshold number of graphic objects associated with the structural variants are densely located within a threshold distance, a region 1312 including the threshold distance may be determined to be a dense region 1312 in which the graphic objects are dense. According to some embodiments, the density of the graphic objects may be calculated based on the area in which at least one graphic object is visualized within a predetermined unit area, and when the calculated density of the graphic objects is equal to or greater than a threshold value, a region including the graphic object may be determined to be a dense region.

In response to determination of the dense region 1312, the first browser may be controlled such that the dense region 1312 is automatically enlarged or zoomed in for a predetermined period of time and is then output, as shown in a second screen 1320 of FIG. 13. As another example, in response to a pointer being located in the dense region 1312, the first browser may be controlled such that the dense region is enlarged or zoomed in and output, as shown in the second screen 1320. As a further example, in response to a pointer being located on a graphic object included in the dense region 1312, the first browser may be controlled such that the dense region is enlarged or zoomed in and output, as shown in the second screen 1320.

According to an embodiment, the dense area 1312 may be visualized using a separate graphic element such that that the user recognizes the dense region 1312. Here, the separate graphic element may include at least one of a color, a pattern, and a shape.

Meanwhile, it may be determined whether user input to select a graphic object included in the dense region 1312 is received. When it is determined that no user input to select a graphic object included in the dense region 1312 is received for a predetermined period of time, the first browser may be controlled such that the enlarged dense region 1312 is reduced to the original size thereof or the zoomed-in dense region 1312 is zoomed out to the original state thereof. That is, when the dense region 1312 is enlarged or zoomed in but a graphic object included in the dense region 1312 is not selected for a predetermined period of time, the dense region 1312 may be returned to the original state thereof.

Additionally or alternatively, when it is detected that the pointer deviates from the dense region 1312 after being located in the dense region 1312, the first browser may be controlled such that the enlarged or zoomed-in dense region 1312 is returned to the original state thereof. That is, when the pointer is moved out of the dense region 1312 after being located in the dense region 1312, the enlarged or zoomed-in dense region 1312 may be reduced or zoomed out to the original size thereof.

Meanwhile, the user-selected region in the first browser may be enlarged. For example, the first information output region 930 and the second information output region 940 of FIG. 9 may be enlarged based on user input. The user may drag the pointer to select a region to be enlarged, and the region selected by the user may be enlarged or zoomed in and output through the first browser. In addition, the user may enlarge or zoom in the desired region through a touch gesture, such as pinch zoom.

Figure 14:
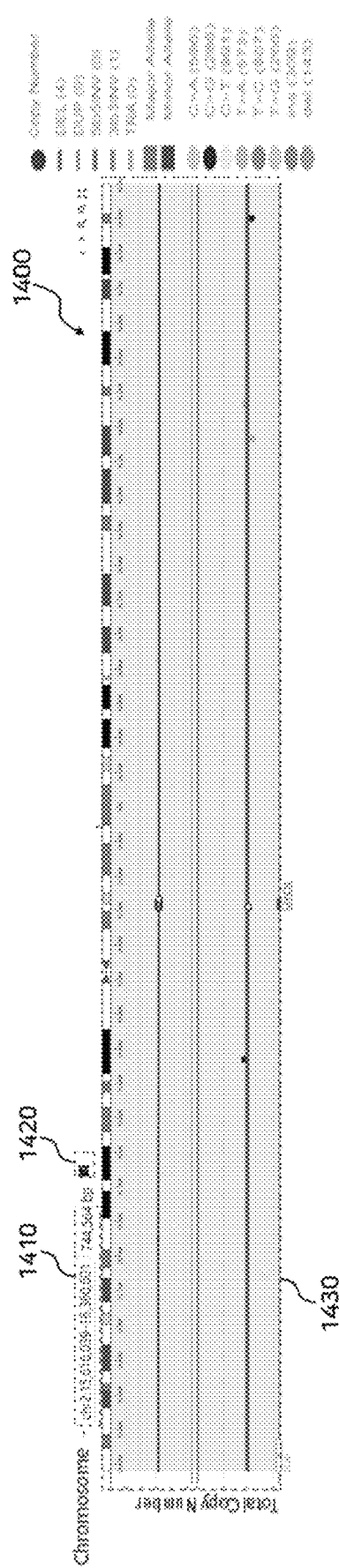
FIG. 14 is a view illustrating an enlarged region in the first browser.

FIG. 14 is a view illustrating an enlarged region 1400 in the first browser. As illustrated in FIG. 14, when a part of the first information output region and/or the second information output region included in the first browser is dragged, the dragged region 1430 may be enlarged or zoomed in and output to the first information output region and/or the second information output region.

FIG. 14 illustrates that a partial region 1430 included in a second chromosome is enlarged or zoomed in and output. As illustrated in FIG. 14, when only a part of the entire region of the base sequence is output, location information 1410 of the output region may be output, and a link icon 1420 configured to provide information associated with the output region may be activated and output.

Meanwhile, a plurality of chromosomes may be selected from among chromosomes included in the genome, and may be output. For example, the chromosome menu included in the menu area 910 illustrated in FIG. 9 may be selected to output a list of chromosomes, and information about a plurality of chromosomes selected from the list of chromosomes may be output through the first browser. When the plurality of chromosomes is selected, the information output region may be divided so as to correspond to the number of chromosomes selected through the first browser, and information associated with each of the plurality of selected chromosomes may be output to a corresponding one of the divided information output region.

Figure 15:
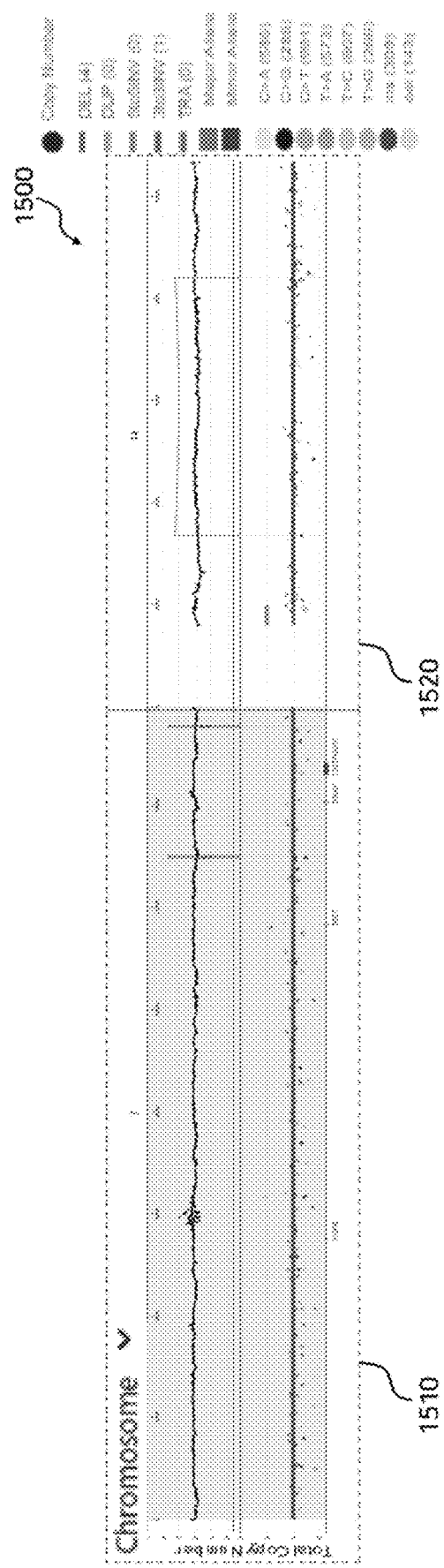
FIG. 15 is a view illustrating a screen of the first browser to which two chromosomes according to an embodiment of the present disclosure are output.

FIG. 15 is a view illustrating a screen 1500 of the first browser to which two chromosomes according to an embodiment of the present disclosure are output. FIG. 15 illustrates that only a seventh chromosome and a fourteenth chromosome are selected and information associated with the seventh chromosome and the fourteenth chromosome is output through the first browser. For example, when a list of chromosomes included in the chromosome menu is output and the seventh chromosome and the fourteenth chromosome are selected from the list of chromosomes, the information output region may be divided into two regions 1510 and 1520 through the first browser. In this case, information associated with the seventh chromosome may be output to the divided first region 1510, and information associated with the fourteenth chromosome may be output to the divided second region 1520.

Meanwhile, one chromosome or three or more chromosomes may be selected from the list of chromosomes included in the chromosome menu, and in this case, information related to the selected number of chromosomes may be output to the information output region.

Meanwhile, a specific type of structural variant is found in a plurality of chromosomes, and information (e.g., visualized information) associated with the specific type of structural variant at the location where the specific type of structural variant is found may be output to the first browser. For example, when a specific type of structural variant is found on both a second chromosome and a fifteenth chromosome, visualization information about the specific type of structural variant may be output to a region associated with the second chromosome and a region associated with the fifteenth chromosome, in the first information output region of the first browser. In the state in which visualization information associated with the specific type of structural variant is located in a plurality of chromosome regions, the first browser may receive user input to select the specific type of structural variant. For example, user input to select visualization information associated with the specific type of structural variant or to select a filter object associated with the specific type of structural variant may be received.

In this case, the first browser may be controlled such that only information related to at least one chromosome on which the specific type of structural variant has been found is output. For example, when user input to select the specific type of structural variant is input in the state in which the specific type of structural variant is found on both the second chromosome and the fifteenth chromosome, the first browser may be controlled such that only information associated with the second chromosome and information associated with the fifteenth chromosome are output from the first browser. In this case, the information output region of the first browser may be divided by the number of relevant chromosomes, and the information associated with each of the chromosomes may be output to a corresponding one of the divided information output regions.

Figure 16:
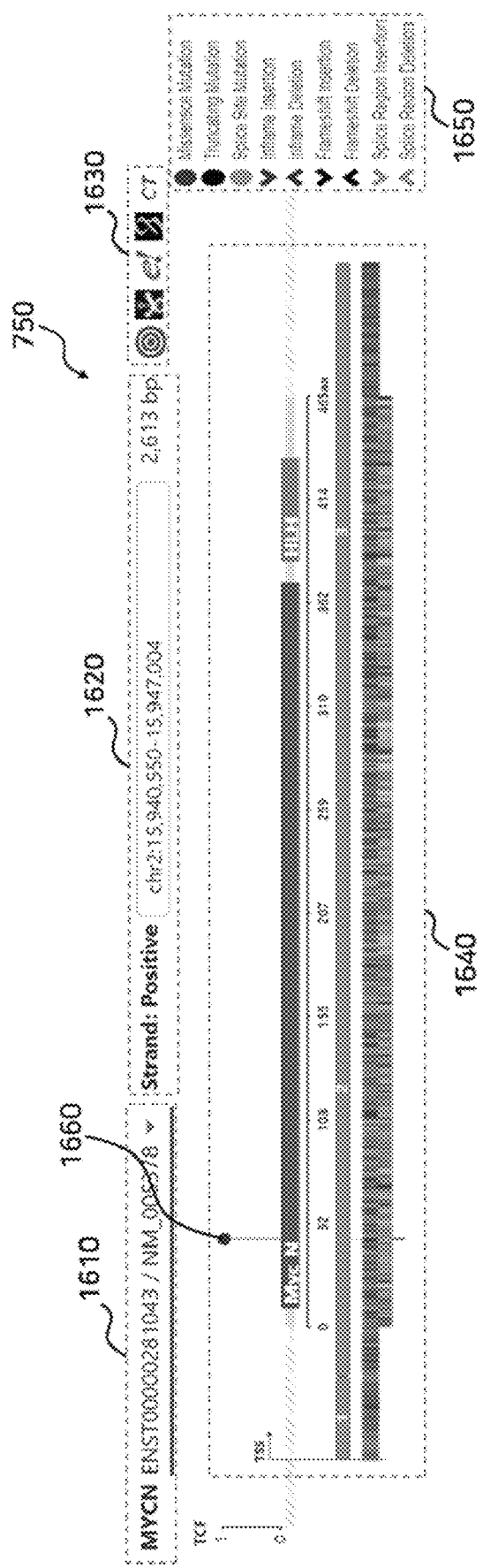
FIG. 16 is a more detailed view of a fifth subregion where the second browser of FIG. 7 is provided.

FIG. 16 is a more detailed view of the fifth subregion 750 where the second browser of FIG. 7 is provided. As illustrated in FIG. 16, the second browser may be configured as a layout including a transcription model region 1610 to which the currently selected transcription model is output, a location information region 1620 to which information about the location of a positive strand in a DNA double helix is output, an icon region 1630 to which link an icon to access an external database is output, an information output region 1640 to which sequence information about the mutation is output, and a description region 1650 that describes a graphic object-specific variant type. Here, the sequence information may include a ribonucleic acid (RNA) sequence to which some regions of the DNA sequence have been transcribed by the transcription model and/or an amino acid sequence translated in response to such sequences.

Identification information (e.g., name) for the currently selected transcription model may be output to the transcription model region 1610, and a location range (coordinate range) of this transcription model may be output to the location information region 1620. When the transcription model is changed, the identification information output to the transcription model region 1610 and the location information output to the location information region 1620 may be changed, and the sequence information output to the information output region 1640 may also be changed.

A link icon to access an external database that provides at least one of a detailed description of a gene output to the information output region 1640 and a well-known mutation associated with the gene, comment information, a treatment method, and effects of the treatment method may be output to the icon region 1630. The method of activating the link icon may be the same as the method of activating the link icon described with reference to FIG. 8.

As described in the description region 1650, variants may be visualized in the information output region 1640 using different graphic objects depending on the type. For example, a missense mutation may be visualized in the information output region 1640 using a first graphic object formed in the shape of a circle having a first color, a truncating mutation may be visualized in the information output region 1640 using a second graphic object formed in the shape of a circle having a second color, and a mutation associated with inframe insertion may be visualized in the information output region 1640 using a third graphic object having a first color and a downward arrow. In addition, as illustrated in the description region 1650, various graphic objects may be used to visualize the variant of the type in the information output region 1640.

A DNA base sequence, an RNA sequence to which the DNA sequence has been transcribed, an amino acid sequence translated according to such sequences, and/or other genetic information may be output to the information output region 1640. Exon associated with the selected gene, a translated amino acid sequence from the base sequence, a base sequence region to be translated, an untranslated region from the base sequence, and domain information may be output to the information output region. A plurality of bases obtained from a specimen may be output to the region of the base sequence to be translated, and both a base in which a variant has occurred and a base of a reference sequence for comparison may be output. A plurality of amino acid identifiers with the bases translated may be output to the amino acid sequence region. In addition, amino acid change information including an amino acid identifier where the variant has occurred and an amino acid identifier at the location corresponding to the amino acid where the variant has occurred in the amino acid sequence according to the reference sequence may be output to the amino acid information region.

Here, the reference sequence may be a base sequence on which the alignment is based. In addition, reference amino acid may be an RNA sequence to which some bases included in the reference sequence are transcribed or an amino acid sequence translated from the RNA sequence. The reference amino acid may be used as baseline information to determine whether an amino acid has been altered. In addition, the reference base may be a base included in the reference sequence, and the reference amino acid identifier may be an amino acid identifier included in the reference amino acid.

Based on information output to the information output region 1640, the user may check how the base sequence is translated into amino acid according to the transcription model and may determine how a variant found in the base sequence of the specimen affects the amino acid sequence.

A section from "0" to "465aa" illustrated in FIG. 16 may be an amino acid region translated from a part of the base sequence. In addition, the numbers "1", "2", and "3" in rectangles illustrated in FIG. 16 may indicate that the DNA has excluded intron regions and numbered exon regions.

In addition, mutation information for the base at the bottom and amino acid information that has changed compared to the reference amino acid may be output to the information output region 1640. That is, amino acid change information indicating the difference between the amino acid to be compared and the reference amino acid may be output to the information output region 1640. When a specific region of the second browser is dragged, the dragged region may be enlarged and output to the information output region 1640. When the output region 1640 is enlarged, characters associated with the amino acid identifier and the base are displayed, whereby the user may identify the changes in the base sequence and the amino acid sequence.

According to an embodiment, a graphic object 1660 may be output to the information output region 1640 in association with the location of the mutation in the selected gene. As previously described, the graphic object 1660 associated with the type of mutation may be output to the information output region 1640.

A pointer may be used to select the graphic object 1660 output to the information output region 1640. That is, user input to select the mutation-related graphic object 1660 output to the information output region 1640 may be received. In response to the user input to select the graphic object 1660, details about that mutation may be output.

Figure 17:
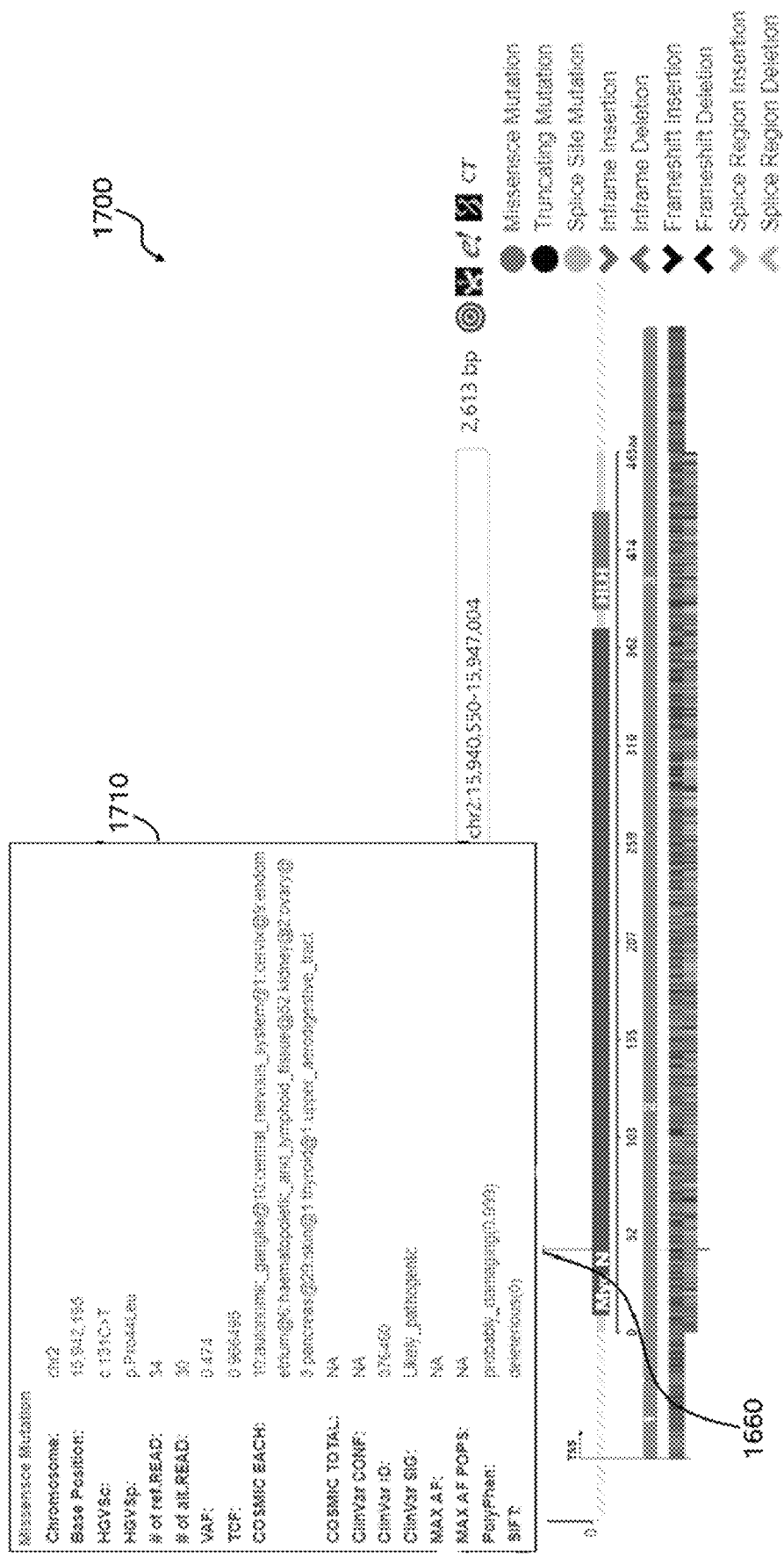
FIG. 17 is a view illustrating a screen to which details of a mutation according to an embodiment of the present disclosure are output.

FIG. 17 is a view illustrating a screen 1700 to which details of a mutation according to an embodiment of the present disclosure are output. As illustrated in FIG. 17, details 1710 about the mutation may be output in response to the user input to select the graphic object 1660 associated with the mutation.

Details 1710 about the analysis results of the mutation may include chromosome information, base position information associated with the location of the mutation, HGVSc information associated with the variation in the DNA, HGVSp information associated with the amino acid variation, "# of ref.READ" information and "# of alt.READ" information associated with the number of counts of the reference allele at that position, a variant allele frequency (VAF) value, and a TCF value. Here, the TCF value is the proportion of a specimen that carries the mutation, which may be an arithmetic inference based on a combination of various pieces of surrounding information. Additionally, the details 1710 of the analysis results of the mutation may include other items, such as COSMIC and ClinVar, PolyPhen, and SIFT. Here, PolyPhen and SIFT may be results of inferring the effect of the variant on the function of the gene based on the degree of conservation of the sequence (e.g., whether the exact same sequence exists in monkeys).

According to an embodiment, user input to request a comparison for a specific mutation associated with the graphic object 1660 may be received. In this case, the information processing system may receive a comparison request for a specific mutation from the user terminal, and in response to receiving the comparison request, the information processing system may identify another specimen included in the project associated with the specimen. Subsequently, the information processing system may extract details of a specific mutation found in the identified other specimen from the database, and may transmit the same to the user terminal. In this case, the user terminal may correlate the details of the specific mutation found in the specimen with the details of the specific mutation found in the other specimen, and may output the same through the user interface. The details about each associated mutation may be output to a single screen through the user interface. Consequently, the user may compare the details about different specimens through the single screen.

Meanwhile, the user terminal may store all pieces of information associated with the project. When user input to request a comparison for a specific mutation associated with the graphic object 1660 is received in the state in which all pieces of information associated with the project are stored in the user terminal, the user terminal may extract genome analysis information for the other specimen from the stored project information and may obtain the details of the specific mutation from the extracted genome analysis information. Subsequently, the user terminal may correlate the details of the specific mutation found in the specimen with the details of the specific mutation found in the other specimen and output the same through the user interface.

Meanwhile, when the graphic object 1660 associated with the mutation is selected, the amino acid region associated with the mutation may be automatically enlarged.

Figure 18:
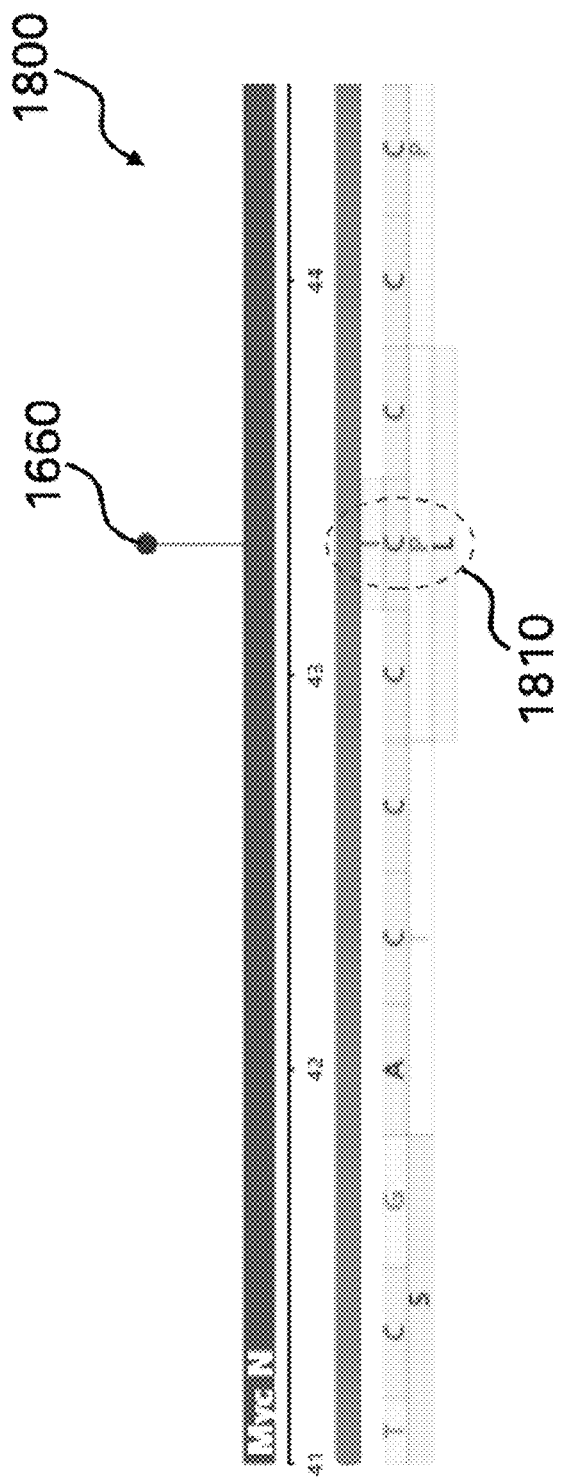
FIG. 18 is a view illustrating an information output region set such that specific regions of a DNA base sequence and an amino acid sequence are displayed in an enlarged state.

FIG. 18 is a view illustrating an information output region 1800 set such that specific regions of a base sequence and an amino acid sequence are displayed in an enlarged state. In response to the user input to select the graphic object 1660 associated with the specific mutation, a specific region of the amino acid sequence and a specific region of the base sequence associated with the specific mutation may be enlarged or zoomed in and displayed. As the specific regions of the amino acid sequence and the base sequence are zoomed in and displayed, a character or an identifier associated with each of a base that is altered and an amino acid identifier may be enlarged and displayed, whereby the user may recognize the base and the amino acid identifier with the naked eye.

Upon determining that the amino acid is different from the reference amino acid, amino acid change information 1810 including an identifier of the reference amino acid and an identifier of the altered amino acid, may be output to the information output region 1800.

In FIG. 18, the amino acid change information 1810 is illustrated as including "C" as a base of the reference sequence, "T" as a base mutated in the specimen, "P" as a reference amino acid identifier, and "L" as an altered amino acid identifier. According to the amino acid change information 1810 of FIG. 18, it may be interpreted that the base of the specimen is changed from "C" to "T" compared to the reference sequence and that the amino acid of the specimen is changed from "P" to "L" compared to the reference amino acid.

The enlarged screen shown in FIG. 18 may also be achieved by dragging a pointer or through a touch gesture. That is, when the region associated with FIG. 18 is dragged using the pointer, the region illustrated in FIG. 18 may be enlarged and output.

A list of transcription models, from which a transcription model can be selected, may be output to the second browser. The list of transcription models may include a plurality of transcription models associated with some regions in the base sequence. For example, when a first region from a first point to a second point in the entire base sequence is selected, a plurality of transcription models capable of transcribing and translating a part or the entirety of the first region may be included in the list of transcription models.

According to an embodiment, the information processing system may transcribe and translate the base sequence obtained from the specimen through each transcription model, and may include the results of translation through each transcription model in the genome analysis information.

Figure 19:
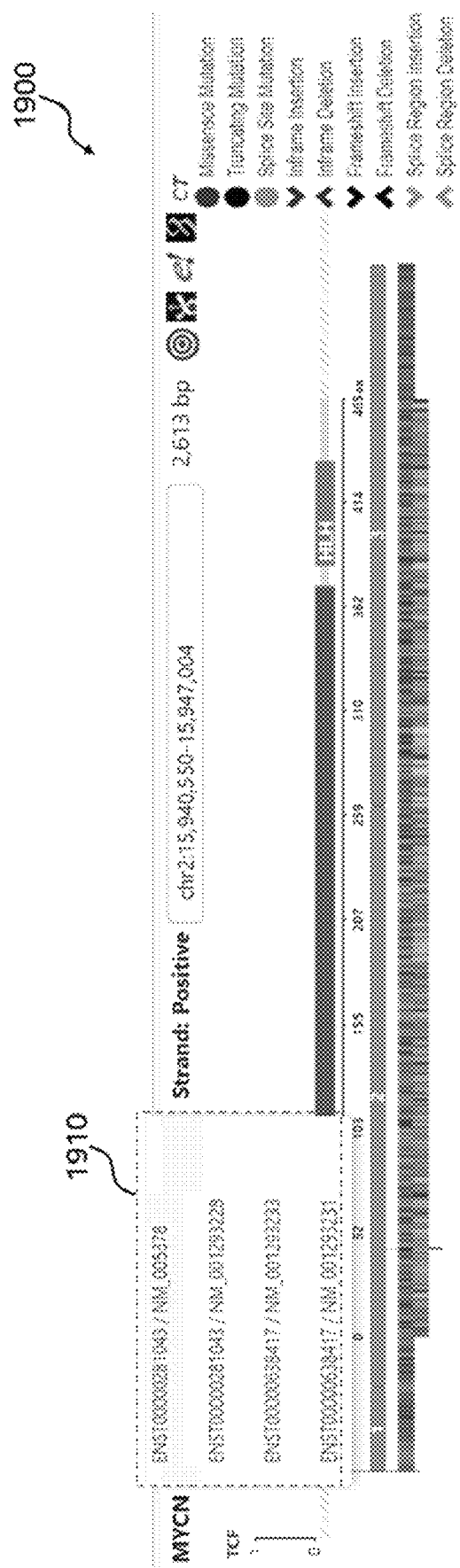
FIG. 19 is a view illustrating the second browser to which a list of transcription models is output.

FIG. 19 is a view illustrating the second browser 1900 to which a list of transcription models is output. In response to receiving user input to request a list of transcription models, a list of transcription models 1910 may be output. In response to receiving user input to select a specific transcription model from among transcription models included in the list of transcription models 1910, the second browser may be controlled such that the results of transcription and translation are reflected by the selected specific transcription model.

Meanwhile, the transcription models may have priorities. The priorities may be predetermined based on conditions such as frequency of use, may be pre-designated by an expert analyst, or may be determined by ascending/descending text.

When the region output to the first browser is changed, the list of transcription models associated with that region may be changed. When the list of transcription models is changed, as described above, a target transcription model to be output to the second browser may be determined based on priorities of the transcription models included in the list of transcription models. That is, based on priorities of transcription models included in the list of transcription models, a transcription model having the highest priority may be determined to be a target transcription model, and the gene information including the results of transcription and translation through the determined target transcription model may be output through the second browser.

Meanwhile, when a specific chromosome is selected in the first browser, the first browser and the second browser may be operated in conjunction with each other based on the selected specific chromosome.

Figure 20:
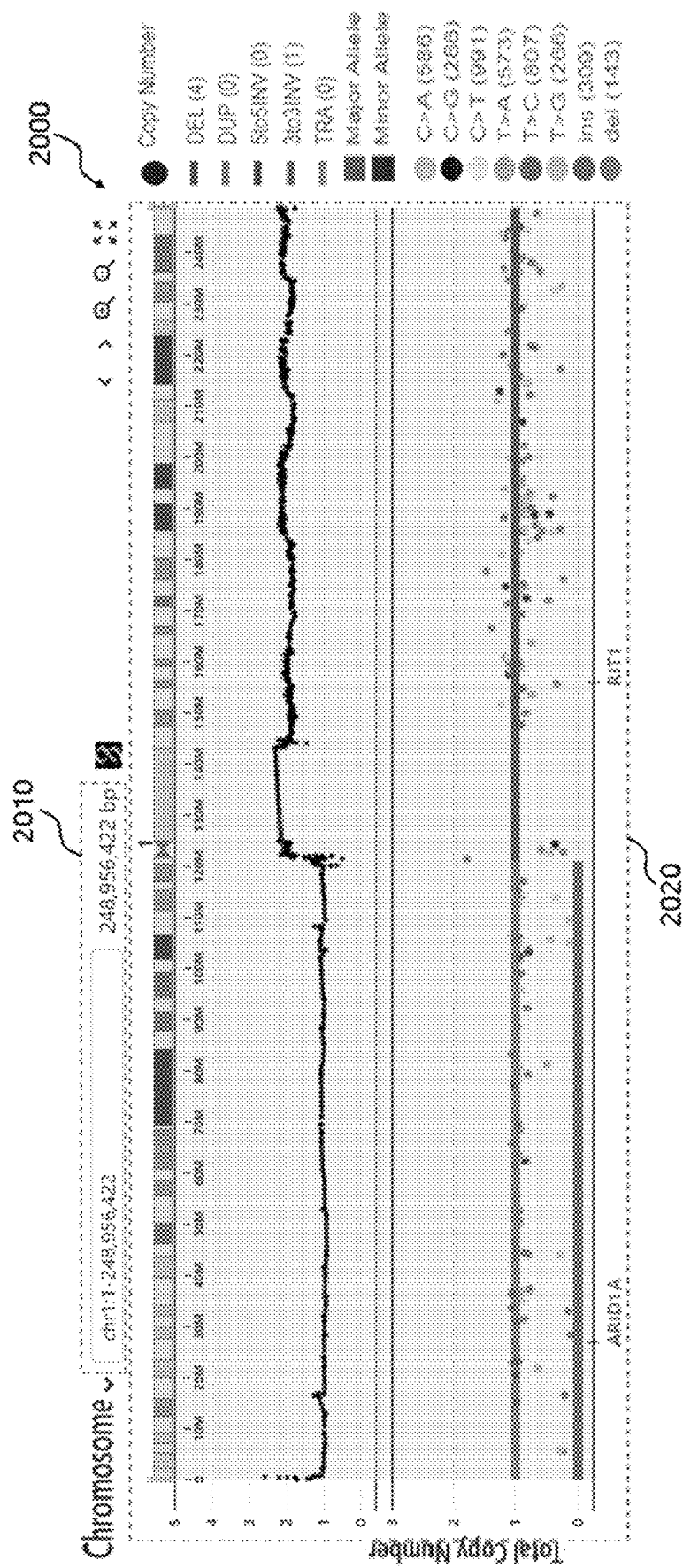
FIG. 20 is a view illustrating a screen of the first browser to which information associated with a specific chromosome according to an embodiment of the present disclosure is output.

FIG. 20 is a view illustrating a screen 2000 of the first browser to which information associated with a specific chromosome according to an embodiment of the present disclosure is output. In FIG. 20, it is illustrated that location information and size-related information 2010 of a first chromosome are output in response to selection of the first chromosome and only information related to first chromosome is selected and output to an information output region 2020.

In response to output of information associated with the first chromosome through the first browser, information output to the second browser may also be changed.

Figure 21:
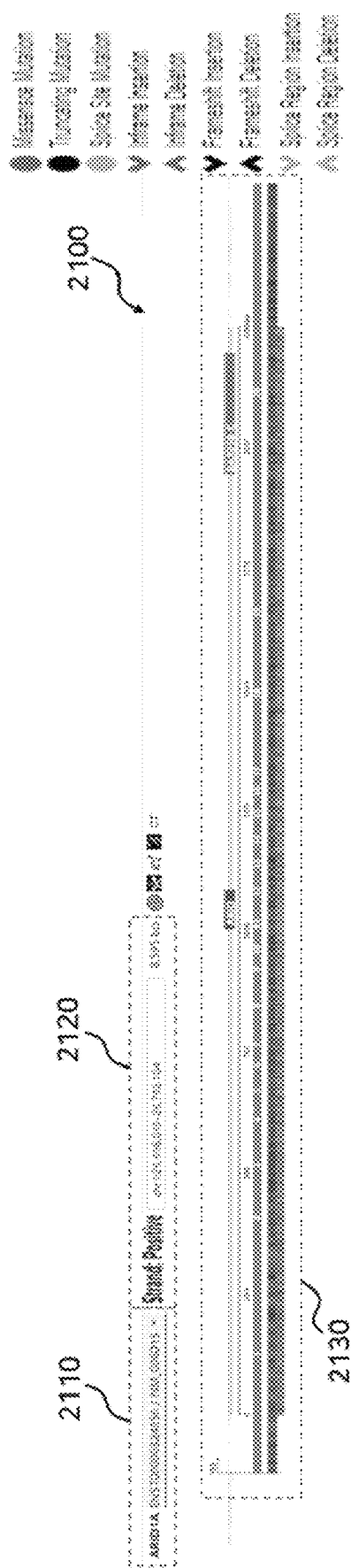
FIG. 21 is a view illustrating a screen of the second browser operated in conjunction with a gene associated with a chromosome selected in the first browser.

FIG. 21 is a view illustrating a screen 2100 of the second browser operated in conjunction with a gene associated with a chromosome selected in the first browser. As illustrated in FIG. 21, a list of transcription models capable of transcribing and translating an "ARID1A" region of a specific gene included in a first chromosome may be obtained, and a target transcription model to be output may be determined based on priorities of transcription models included in the list of transcription models.

Information 2110 related to the determined target transcription model may be output through the second browser. In addition, information 2120 related to a region and size transcribed and translated through the target transcription model may be output through the second browser. In addition, genetic information 2130 including the results of transcription and translation by the target transcription model may be output through the second browser.

When a specific chromosome is selected in the first browser, as described above, genetic information associated with the specific chromosome may be output to the second browser.

Meanwhile, when specific mutation information/gene label is selected from the list of drivers, the first browser and the second browser may be controlled such that information associated with the selected mutation information/gene label is output.

Figure 22:
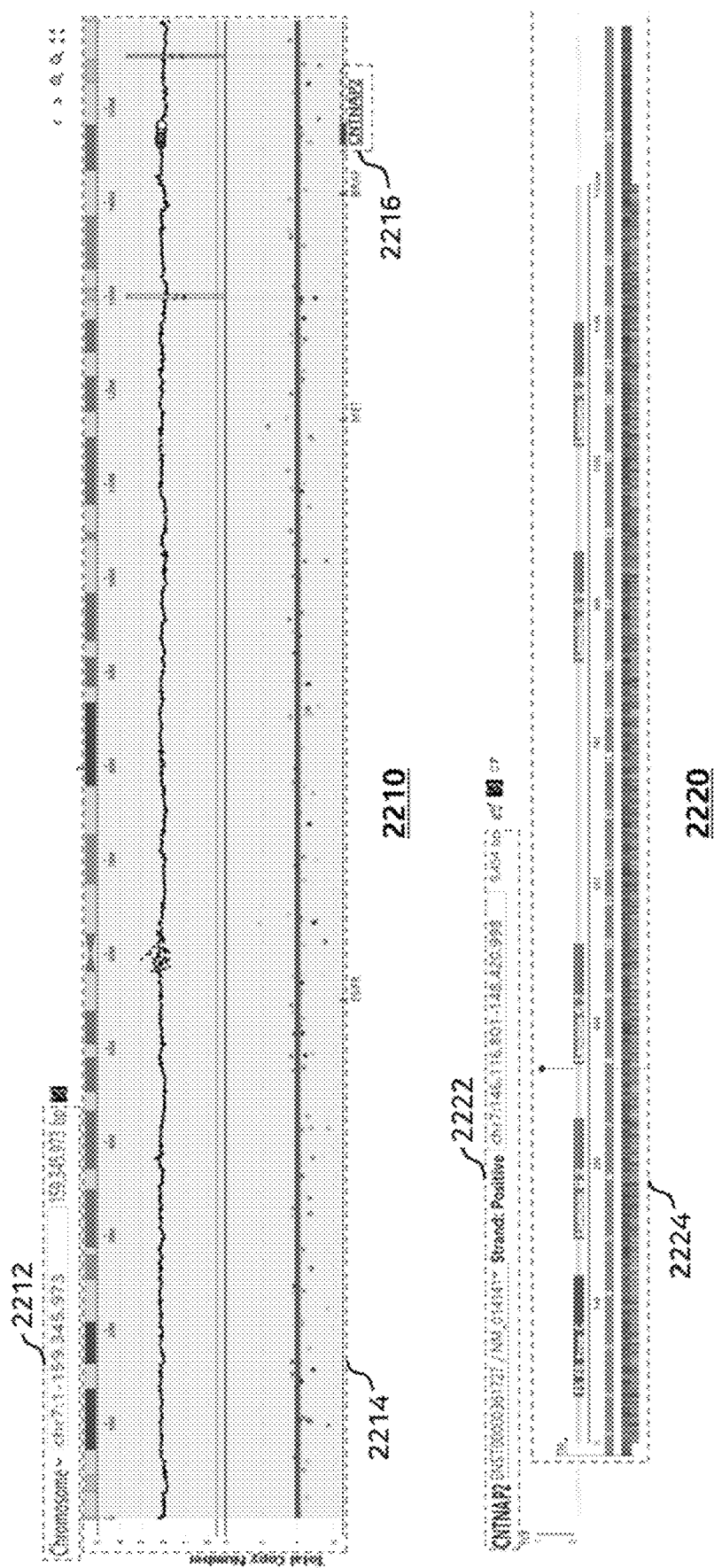
FIG. 22 is a view illustrating a screen of the first browser and a screen of the second browser operated based on mutation information selected from a list of drivers.

FIG. 22 is a view illustrating a screen 2210 of the first browser and a screen 2220 of the second browser operated based on mutation information selected from the list of drivers. For example, in response to user input to select "CNTNAP2" and/or mutation information related to "CNTNAP2" from the list of drivers, only information related to a seventh chromosome where the "CNTNAP2" gene is located may be output to an information output region 2214 through the first browser. That is, when the user selects "CNTNAP2" and/or a mutation related to "CNTNAP2" from the list of drivers, only the seventh chromosome where the "CNTNAP2" gene is found may be selected and output to the information output region 2214 through the first browser. Information 2212 indicating that the chromosome associated with the "CNTNAP2" gene is the seventh chromosome may be output through the first browser, and "CNTNAP2" 2216, which is a gene label, may also be output through the first browser.

In addition, a list of transcription models associated with the region of the seventh chromosome where the "CNTNAP2" gene is located may be obtained, and a target transcription model may be determined based on priorities of transcription models included in the list of transcription models. Genetic information including the results of transcription and translation by the target transcription model may be output to an information output region 2224 through the second browser. In addition, information 2222 including identification information of the target transcription model and a location region translated by the target transcription model may be output through the second browser.

The information output to each of the first and second browsers may be changed by selecting the mutation information/gene label included in the list of drivers, as described above.

Figure 23:
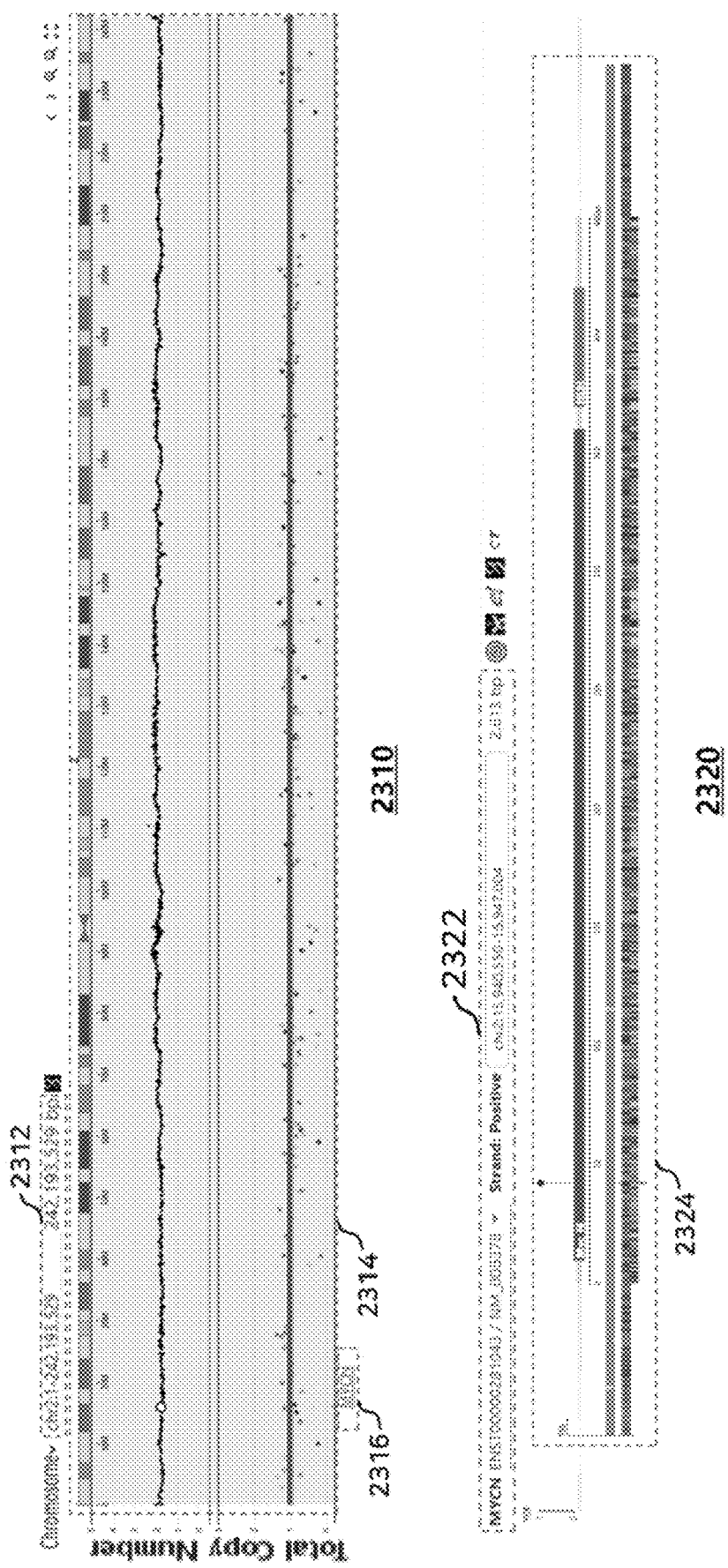
FIG. 23 is a view illustrating another example of the screen of the first browser and the screen of the second browser operated based on the mutation information selected from the list of drivers.

FIG. 23 is a view illustrating another example of a screen 2310 of the first browser and a screen 2320 of the second browser operated based on the mutation information selected from the list of drivers. For example, in response to user input to select "MYON" and/or mutation information related to "MYON" from the list of drivers, only information related to the second chromosome where the "MYON" gene is located may be output to an information output region 2314 through the first browser. Information 2212 indicating that the chromosome associated with the "MYON" gene is the second chromosome may be output through the first browser, and "MYON" 2316, which is a gene label, may also be output through the first browser.

In addition, a list of transcription models associated with the region of the second chromosome where the "MYON" gene is located may be obtained, and a target transcription model may be determined based on priorities of transcription models included in the obtained list of transcription models. Genetic information including the results of transcription and translation by the target transcription model may be output to an information output region 2324 through the second browser. In addition, information 2322 including identification information of the target transcription model and a location region translated by the target transcription model may be output through the second browser.

Figure 24:
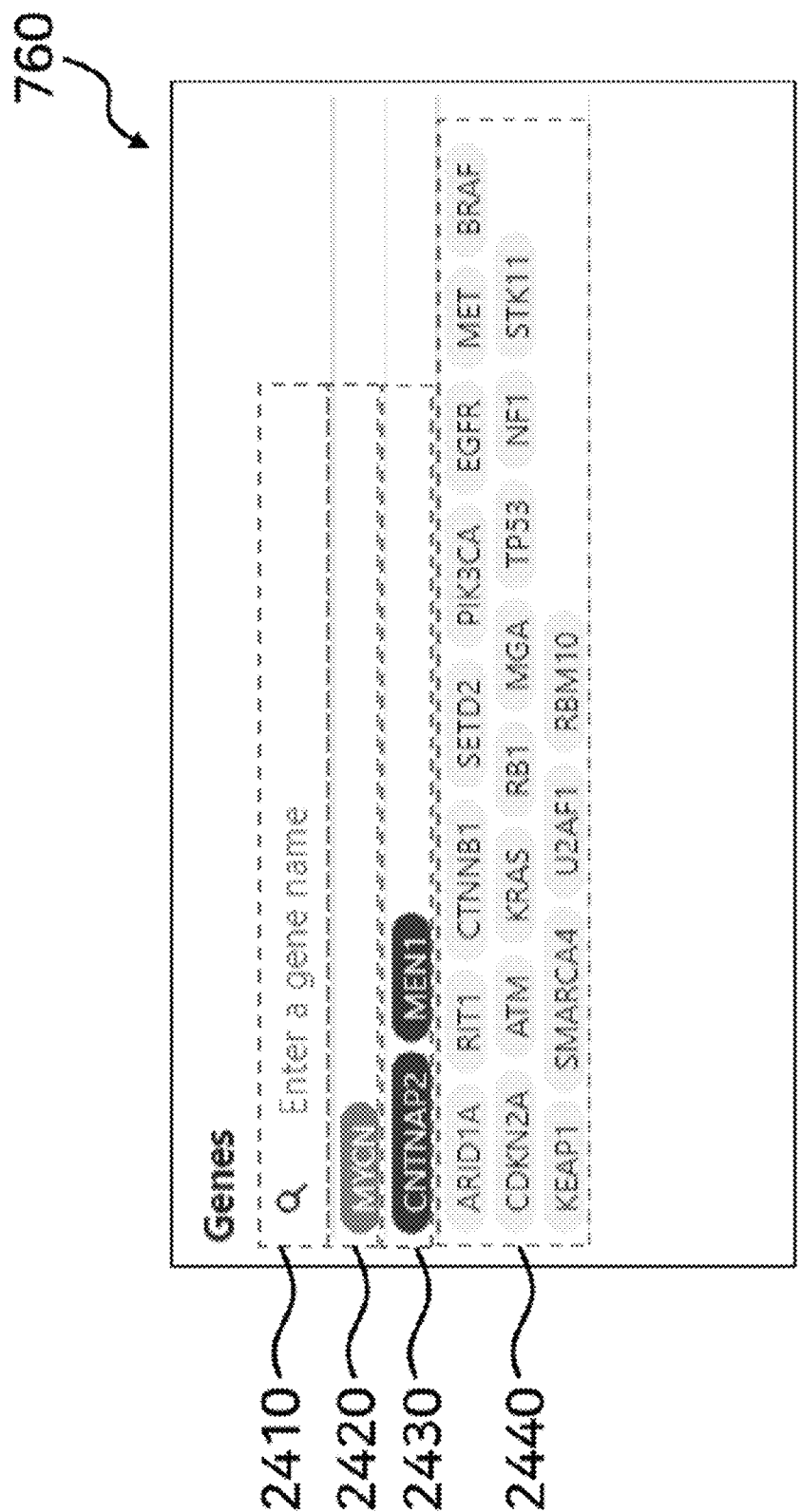
FIG. 24 is an enlarged view of a sixth subregion of FIG. 7.

FIG. 24 is an enlarged view of the sixth subregion 760 of FIG. 7. As illustrated in FIG. 24, i.e., as illustrated in the enlarged sixth subregion 760, a list of genes 2420 to 2440 with major mutations associated with a specific disease may be output. For example, the list of genes 2420 to 2440 may include labels of genes in which representative mutations associated with specific cancer are found.

An input field 2410 in which major genes may be added may be output to the sixth subregion 760. The user may add a gene label associated with a specific mutation to the list of genes by entering a gene label into the input field 2410.

The list of genes 2420 to 2440 may include gene labels visualized using graphic elements having different gene types. According to an embodiment, a gene label 2420 found in the specimen and included in the list of oncogene drivers, among genes included in the list of genes, may be visualized using a first graphic element and may be output to the sixth subregion 760. In addition, a gene label 2430 found in the specimen and included in the list of tumor suppressor drivers, among the genes included in the list of genes, may be visualized using a second graphic element and may be output to the sixth subregion 760. Furthermore, a gene label 2440 associated with a mutation not found in the specimen, among the genes included in the list of genes, may be visualized using a third graphic element and may be output to the sixth subregion 760. In FIG. 24, it is illustrated that the first graphic element is a first color, the second graphic element is a second color, and the third graphic element is a third color.

Although not shown in the figure, a gene label added to the list of genes through the input field 2410 may be visualized using a fourth graphic element and may be output to the sixth subregion 760.

According to an embodiment of the present disclosure, when a specific gene label included in the list of genes is selected, information of each of the first browser and the second browser may be changed in conjunction with each other based on the selected specific gene label.

Figure 25:
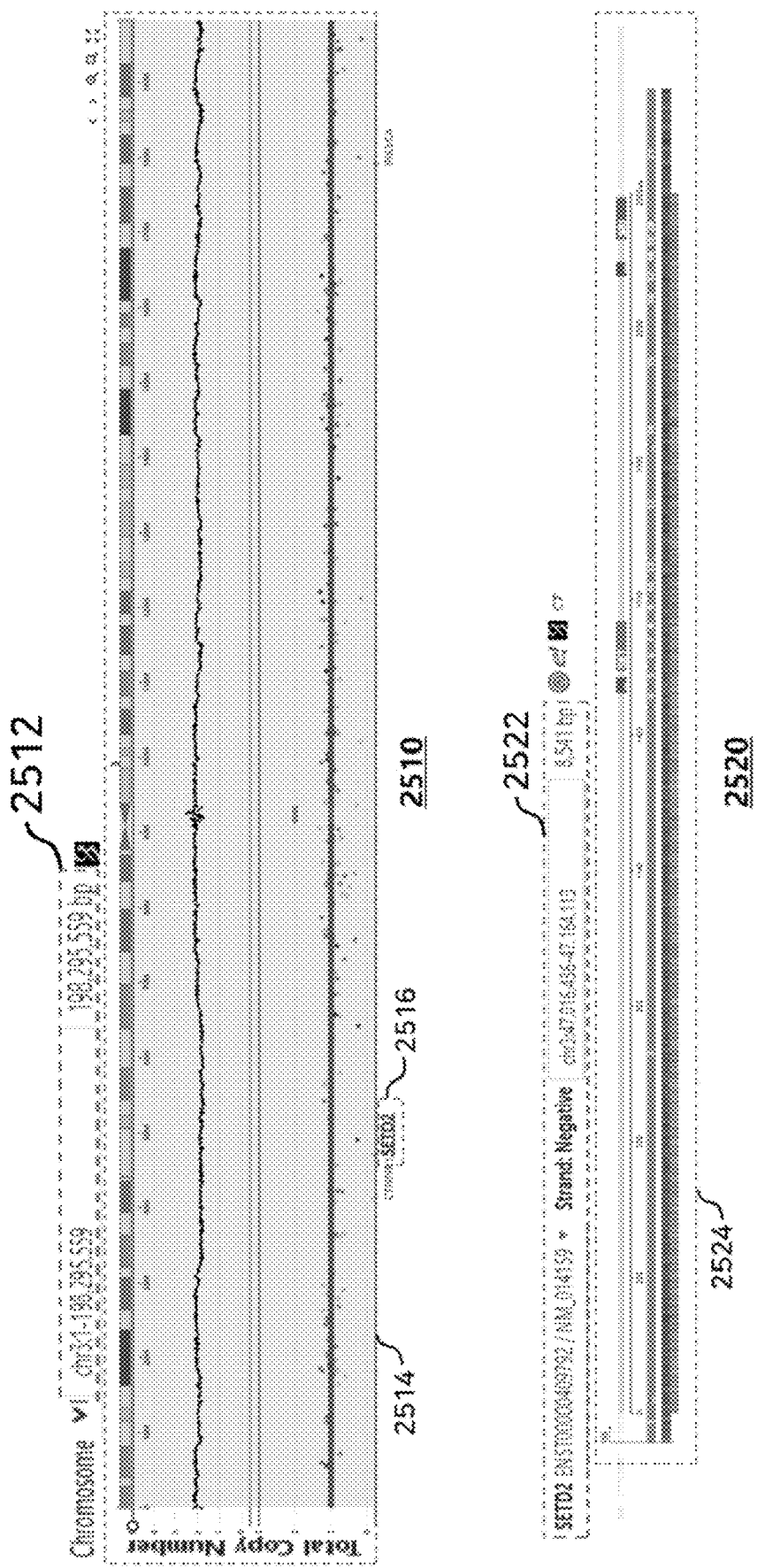
FIG. 25 is a view illustrating a screen of the first browser and a screen of the second browser operated based on a gene selected from a list of genes according to an embodiment of the present disclosure.

FIG. 25 is a view illustrating a screen 2510 of the first browser and a screen 2520 of the second browser operated based on a gene selected from a list of genes according to an embodiment of the present disclosure. For example, in response to user input to select "SETD2" from the list of genes, information related to a third chromosome where the "SETD2" gene is located may be output to an information output region 2514 through the first browser. Here, it should be noted that "SETD2" is a gene for which no mutation was found in the specimen. That is, according to the embodiment of the present disclosure, the list of genes may also include labels of major genes where no mutation is found in the specimen, and accordingly, user input to select the "SETD2" gene where no mutation is found in the specimen from the list of genes may be received.

In this case, the third chromosome where the "SETD2" gene is located may be selected and output to the information output region 2514 through the first browser. Information 2512 about the third chromosome where the "SETD2" gene is located may be output through the first browser, and a label 2516 of the "SETD2" gene may also be output through the first browser.

In addition, a list of transcription models used to transcribe and translate the "SETD2" gene region may be obtained, and a target transcription model may be determined based on priorities of transcription models included in the list of transcription models. Genetic information including results translated by the target transcription model may be output to an information output region 2524 through the second browser. In addition, information 2522 including identification information of the target transcription model and a location region translated by the target transcription model may be output through the second browser.

The information output to each of the first and second browsers may be changed by selecting the mutation included in the list of major mutations, as described above.

Figure 26:
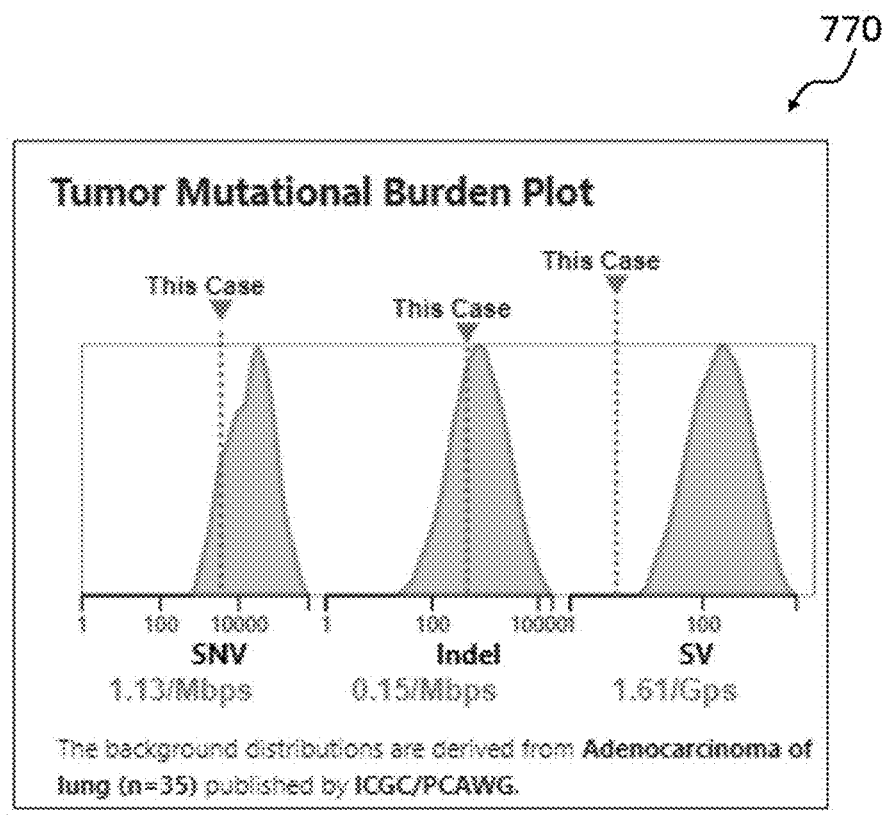
FIG. 26 is an enlarged view of a seventh subregion of FIG. 7.

FIG. 26 is an enlarged view of the seventh subregion 770 of FIG. 7. As illustrated in FIG. 26, information associated with a plot of tumor mutational burden of the specimen (hereinafter referred to as a "tumor mutational burden plot") may be output to the seventh subregion 770. Here, the information associated with the plot of tumor mutational burden may include statistical information about different types of variants.

For example, mutational burden statistical information of tumor mutational burden for each of a single nucleotide variation, an indel (insertion & deletion), and structural variants (SVs) found in the specimen may be calculated and output to the seventh subregion 770 in the form of a graph. That is, a tumor mutational burden plot for a single nucleotide variation (SNV) in the specimen may be calculated, and a graphic element (in FIG. 26, This Case) associated with the calculated tumor mutational burden plot for the single nucleotide variation (SNV) may be output from a single nucleotide variation (SNV) distribution graph. In FIG. 26, the tumor mutational burden plot for the single nucleotide variation (SNV) is illustrated as being calculated to be 1.13/Mbps.

In addition, a tumor mutational burden plot for an indel found in the specimen may be calculated, and a graphic element (in FIG. 26, This Case) associated with the calculated tumor mutational burden plot for the indel may be output from an indel distribution graph. In FIG. 26, the tumor mutational burden plot for the indel is illustrated as being calculated to be 0.15/Mbps.

Additionally, a tumor mutational burden plot for structural variants (SVs) found in the specimen may be calculated, and a graphic element (in FIG. 26, This Case) associated with the calculated tumor mutational burden plot for the structural variants may be output from a structural variant distribution graph. In FIG. 26, the tumor mutational burden plot for the structural variants is illustrated as being calculated to be 1.61/Mbps.

Meanwhile, in some embodiments, user input to request a comparison of tumor mutational burden may be received through the user interface. In this case, the information processing system may receive a comparison request for tumor mutational burden from the user terminal, and in response to receiving the comparison request, may identify the other specimen from the project including the specimen or from all projects stored in the information processing system 230. Subsequently, the information processing system may extract information associated with a tumor mutational burden plot for the identified other specimen from the database and transmit the same to the user terminal. Subsequently, the user terminal may correlate information related to the tumor mutational burden plot for the specimen with information related to the tumor mutational burden plot for the other specimen and output the same through the user interface. Information about the tumor mutational burden plots for the specimen and the other specimen correlated with each other may be output to a single screen through the user interface. For example, statistical information related to the tumor mutational burden plot for the other specimen and statistical information related to the tumor mutational burden plot for the specimen (e.g., statistical information related to FIG. 26) may be output to the user interface so as to be compared on a single screen.

Meanwhile, all pieces of information associated with the project may be stored in the user terminal. When user input to request a comparison of tumor mutational burden is received in the state in which all pieces of information associated with the project are stored in the user terminal, information associated with the tumor mutational burden plot for the other specimen may be extracted from the stored project information. Subsequently, the user terminal may correlate information related to the tumor mutational burden plot for the specimen with information related to the tumor mutational burden plot for the other specimen, and may output the same through the user interface.

Figure 27:
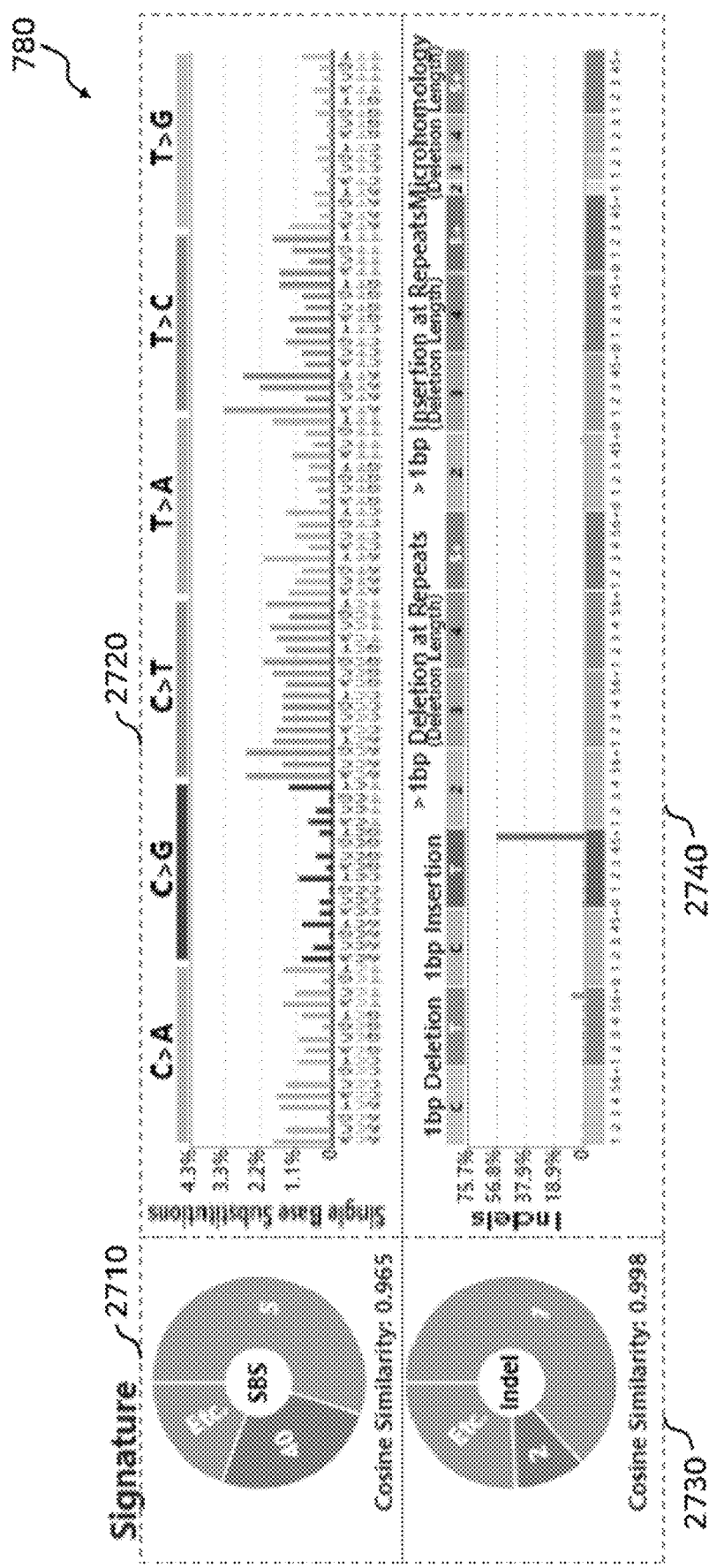
FIG. 27 is an enlarged view of an eighth subregion of FIG. 7.

FIG. 27 is an enlarged view of the eighth subregion 780 of FIG. 7. As illustrated in FIG. 27, mutational signature information for the specimen may be output to the eighth subregion 780. The mutational signature information may include SBS mutation information and indel mutation information. As illustrated in FIG. 27, information 2710 to 2740 output to the fourth subregion 780 may be output in the form of a graph.

As illustrated in FIG. 27, first SBS mutation information 2710 including the percentage occupied by each SBS category may be output to the eighth subregion 780. Here, the SBS categories may include SBS1, SBS4, SBS5, and SBS40. In FIG. 27, it is illustrated that SBS mutations found in the specimen are SBS1, SBS4, SBS5, and SBS40, the percentage of the total SBS occupied by each of SBS1, SBS4, SBS5, and SBS40 is calculated, and the calculated percentages are output in the form of a donut chart. In FIG. 27, SBS4 and SBS1 are illustrated as being included in an Etc. region, and when a pointer is moved to the Etc. region and then clicked on (or touched), the percentages of SBS4 and SBS1 may be output from the donut chart.

In addition, cosine similarity between reference SBS mutation information and the SBS mutation information analyzed from the specimen may be calculated, and the calculated SBS cosine similarity may be included in the first SBS mutation information 2710. Here, the reference SBS mutation information is information based on which the SBS cosine similarity is calculated, and may be pre-stored in the information processing system and/or the user terminal, or may be stored in any storage medium accessible by the information processing system and/or the user terminal. In FIG. 27, the SBS cosine similarity is illustrated as being 0.965.

Additionally, mutations associated with SBS may be categorized according to mutation types (i.e., O>A, O>G, O>T, T>A, T>0, and T>G), and second SBS mutation information 2720 including a percentage of each of the categorized mutation types may be output to the eighth subregion 780. As shown in FIG. 27, a bar graph representing a percentage by SBS mutation type may be included in the second SBS mutation information 2720 and output to the eighth subregion 780.

In addition, first indel mutation information 2730 including a percentage occupied by each indel category may be output to the eighth subregion 780. Here, the indel categories may include various indels, such as ID1, ID2, ID3, ID4, ID5, and ID6. In FIG. 27, it is illustrated that indel mutations found in the specimen are ID1, ID2, ID3, ID4, ID5, ID6, ID9, ID10, ID12, ID14, ID17, and ID18, the percentage of each indel in the total indels is calculated, and the calculated percentage is output to the eighth subregion 780 in the form of a donut chart. In FIG. 27, indel mutations other than ID2 and ID7 are illustrated as being included in an Etc. region, and when a pointer is moved to the Etc. region and then clicked (or touched), the percentages of indel mutations other than ID2 and ID7 may be output from the donut chart.

Additionally, cosine similarity between reference indel mutation information and indel mutation information analyzed from the specimen may be calculated, and the calculated indel cosine similarity may be included in the first indel mutation information 2730. Here, the reference indel mutation information is information based on which the indel cosine similarity is calculated, and may be pre-stored in the information processing system and/or the user terminal. In FIG. 27, the indel cosine similarity is illustrated as being 0.998.

In addition, mutations associated with indels may be categorized according to mutation types (i.e., 1 bp deletion and 1 bp insertion), and second indel mutation information 2740 including a percentage of each of the categorized mutation types may be output to the eighth subregion 780. As shown in FIG. 27, a bar graph representing a percentage by indel mutation type may be output to the eighth subregion 780.

Figure 28:
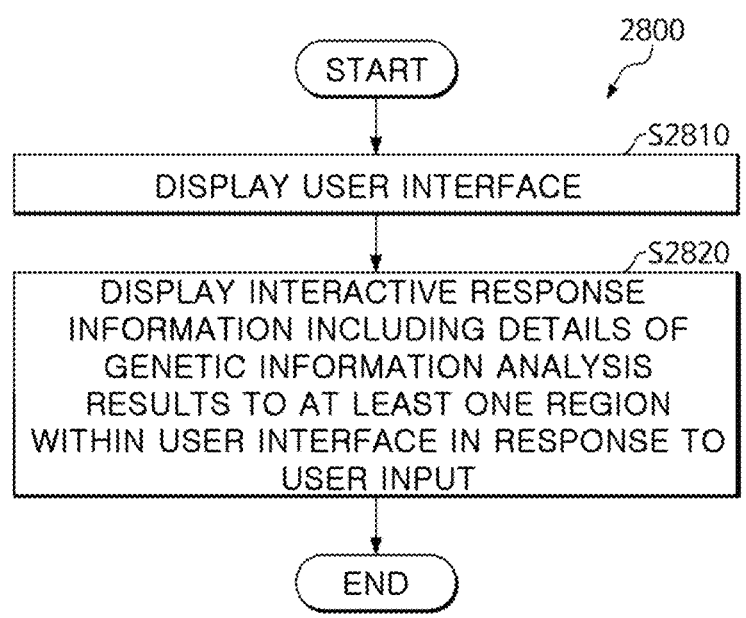
FIG. 28 is a flowchart for describing a method of providing genetic information analysis results according to an embodiment of the present disclosure.

FIG. 28 is a flowchart for describing a method 2800 of providing genetic information analysis results according to an embodiment of the present disclosure. The method shown in FIG. 28 is only one embodiment to accomplish the objects of the present disclosure, and some steps may be added or deleted as needed. In addition, the method shown in FIG. 28 may be performed by at least one processor included in the information processing system and/or at least one processor included in the user terminal. For convenience of description, steps shown in FIG. 28 will be described as being performed by the processor included in the user terminal shown in FIG. 3.

The processor may output a user interface configured to provide genetic information analysis results of a specimen (S2810). According to an embodiment, a list of genes associated with a specific disease may be output to, or displayed in, a first region included in the user interface, and a first browser configured to visualize and search for information regarding a variant obtained by analysis of the specimen may be output to a second region included in the user interface. In addition, a second browser configured to search for sequence information obtained by analysis of the specimen may be output to a third area included in the user interface. According to an embodiment, the first browser and the second browser may be operated in conjunction with each other.

Subsequently, in response to user input received through the user interface, the processor may output interactive response information including details of the genetic information analysis results to at least one region included in the user interface (S2820).

According to an embodiment, the processor may receive user input to select a gene where a specific mutation is identified from the list of genes output to the first region. Subsequently, the processor may control the first browser such that a region of the selected gene is output in response to the user input to select the gene. In addition, the processor may control the second browser such that a region within the sequence information corresponding to the selected gene is displayed in response to the user input to select the gene where the specific mutation is identified.

According to an embodiment, a graphic object indicating the location of the specific mutation may be output, or displayed, in the region in the second browser. In response to receiving user input to select the graphic object, the processor may output details regarding the specific mutation in the genetic information analysis results of the specimen through the second browser.

According to an embodiment, the processor may obtain a list of transcription models associated with a gene where a specific mutation is found, may determine a target transcription model to be output based on priorities of a plurality of transcription models included in the list of transcription models, and may control the second browser such that amino acid sequence information including results transcribed and translated through the determined target transcription model is output.

According to an embodiment, upon determining that first amino acid associated with the gene is different from second amino acid translated from a reference sequence, the processor may control the second browser such that amino acid change information indicating the difference between the first amino acid and the second amino acid is output. Here, the amino acid change information may be output in relation to the location of the specific mutation in the sequence information.

According to an embodiment, the processor may control the second browser such that a list of transcription models is output. Subsequently, in response to receiving user input to select a specific transcription model from the list of transcription models, the processor may control the second browser such that amino acid sequence information including results transcribed and translated through the specific transcription model is output.

According to an embodiment, a specific disease may be identified based on a disease code included in patient information, and the list of genes may include at least one gene whose mutations are associated with the specific disease among mutations found in the specimen.

The specific disease is a disease associated with cancer, and the list of genes may include a list of first drivers including at least one oncogene whose mutations are associated with causing the disease among the mutations found in the specimen, and a list of second drivers including at least one tumor suppressor gene whose mutations are associated with suppressing the disease among the mutations found in the specimen. According to an embodiment, the processor may visualize the label of at least one gene included in the list of first drivers in a first region using a first graphic element, and may visualize the label of at least one gene included in the list of second drivers in the first region using a second graphic element.

According to an embodiment, a graphic object associated with the location of the specific mutation may be output in the region output to the second browser. Also, in response to receiving user input to select the graphic object, the processor may control the second browser such that a region of the sequence information associated with the specific mutation is enlarged and output from the sequence information. A character associated with at least one of the base and the amino acid identifier in which the mutation occurred may be displayed in the enlarged region.

According to an embodiment, after receiving a user comment through a comment field included in a fourth region of the user interface, the processor may provide the received user comment to at least one other user who is participating in a project associated with the specimen.

According to an embodiment, the processor may obtain first information associated with a plot of tumor mutational burden for the specimen, and may output the obtained first information to a fifth region of the user interface. The first information may include tumor mutational burden statistics for at least one of a single nucleotide variation for the specimen, an indel for the specimen, and structural variants for the specimen.

According to an embodiment, the processor may obtain second information associated with a plot of tumor mutational burden for another specimen, and may correlate the first information and the second information with each other and may output the same.

According to an embodiment, in response to receiving user input to request a comparison of a specific mutation among mutations detected in the specimen, the processor may obtain details of a specific mutation detected in the other specimen. Subsequently, the processor may correlate the details of the specific mutation found in the specimen with the details of the specific mutation found in the other specimen and may output the same.

According to an embodiment, an input field into which a gene name or a gene identifier is entered may be output to the first region. In response to receiving the gene name entered through the input field, the processor may add a gene with the received name to the list of genes.

According to an embodiment, the processor may receive user input to select a specific chromosome or a specific gene through the first browser. In response to the user input to select the specific chromosome or the specific gene, the processor may control the second browser such that a region corresponding to the selected specific chromosome or specific gene is output from the sequence information. Also, in response to receiving the user input to select the specific chromosome or the specific gene, the processor may control the first browser such that only a region corresponding to at least one chromosome associated with the specific chromosome or the specific gene is output.

According to an embodiment, the labels of genes associated with a plurality of mutations detected in the specimen may be output in relation to the location of each gene. For example, the label of a gene associated with a mutation associated with causing a disease may be visualized using a first graphic element, and the label of a gene associated with a mutation associated with suppressing the disease may be visualized using a second graphic element. In addition, the label of a gene associated with a mutation not found in the specimen from the list of mutations associated with the disease may be visualized using a third graphic element through the first browser.

According to an embodiment, structural variants detected in the specimen may be visualized using a number of graphic objects corresponding to the number of structural variants through the first browser. The first browser may determine at least one of the shape, color, and size of the graphic object based on the type of a target structural variant to be represented. The graphic object may be visualized in a range corresponding to a region of the target structural variant through the first browser.

According to an embodiment, the processor may determine whether more than a threshold number of graphic objects are located within a threshold distance.

For example, in response to determining that more than a threshold number of graphic objects are located within the threshold distance and that a pointer is located on a specific graphic object included within the threshold distance, the processor may control the first browser such that the specific graphic object where the pointer is located is highlighted and visualized. Additionally or alternatively, the processor may control the first browser such that graphic objects other than the specific graphic object at which the pointer is located, among the graphic objects included within the threshold distance, are removed or blurred.

As another example, in response to determining that more than a threshold number of graphic objects are located within the threshold distance, the processor may control the first browser such that graphic objects that located within the threshold distance are highlighted and visualized while being rotated at predetermined time intervals.

As a further example, in response to determining that more than a threshold number of graphic objects are located within the threshold distance, the processor may determine that a region including the threshold distance is a dense region, and may control the first browser such that the dense region is enlarged when a pointer is detected to be located in the dense region. The processor may control the first browser such that the dense region is visualized using a fourth graphic element. Also, in response to determining whether user input to select a graphic object included in the dense region is received and determining that no user input to select the graphic object included in the dense region is received for a predetermined period of time, the processor may control the first browser such that the enlarged dense region is reduced to the original size thereof. Upon detecting that the pointer deviates from the dense region after the dense region is enlarged, the processor may control the first browser such that the enlarged dense region is reduced to the original size thereof.

According to an embodiment, in response to receiving user input to select a plurality of chromosomes through the first browser, the processor may control the first browser such that information associated with the selected plurality of chromosomes is output. In this case, the first browser may divide an information output region into a number of regions corresponding to the number of selected chromosomes, and may output information associated with each of the selected plurality of chromosomes to a corresponding one of the divided regions.

According to an embodiment, information about at least one structural variant may be output to the first browser, and in response to receiving user input to select a specific structural variant, the processor may control the first browser such that only information associated with at least one chromosome on which the selected specific structural variant is found is output.

According to an embodiment, variant type-specific filter objects may be output to the user interface. The processor may receive user input to select at least one filter object from among the output variant type-specific filter objects, and in response to receiving the user input to select the at least one filter object, may control the first browser such that only information about a variant corresponding to the selected filter object is selected and output from the obtained information about the variant.

The flowchart and description above are illustrative only and may be implemented differently in some embodiments. For example, in some embodiments, the order of the steps may be changed, some steps may be performed repeatedly, some steps may be omitted, or some steps may be added.

The method described above may be provided as a computer program stored on a computer-readable recording medium for execution on a computer. The medium may be a continuous storage of a computer-executable program, or may be a temporary storage for execution or download. In addition, the medium may be any of a variety of recording or storage means in the form of a single or combined piece of hardware, and may be distributed over a network, rather than being limited to a medium that is directly connected to a certain computer system. Examples of the medium may include a magnetic medium, such as a hard disk, a floppy disk, or a magnetic tape, an optical recording medium, such as CD-ROM or DVD, a magneto-optical medium, such as a floptical disk, and a device configured to store program commands, such as ROM, RAM, or flash memory. Other examples of the medium may include a recording medium and a storage medium managed by an app store that distributes applications, a site that provides or distributes various other kinds of software, or a server.

The method, operation, or techniques of the present disclosure may be implemented by a variety of means. For example, the techniques may be implemented as hardware, firmware, software, or a combination thereof. Those skilled in the art will understand that the various exemplary logical blocks, modules, circuits, and algorithmic steps described in connection with the present disclosure may be implemented in electronic hardware, computer software, or a combination thereof. In order to clearly describe interchangeability between hardware and software, various exemplary components, blocks, modules, circuits, and steps have been described above generally in terms of functionality. Whether such functionality is implemented as hardware or software depends on a specific application and design requirements imposed on the overall system. Those skilled in the art may implement functions described in various ways for each specific application, but such implementation should not be construed as departing from the scope of the present disclosure.

In a hardware implementation, processing units used to perform the techniques may be implemented in one or more ASICs, DSPs, digital signal processing devices (DSPDs), programmable logic devices (PLDs), field programmable gate arrays (FPGAs), processors, controllers, microcontrollers, microprocessors, electronic devices, other electronic units designed to perform the functions described in the present disclosure, computers, or combinations thereof.

Accordingly, the various exemplary logic blocks, modules, and circuits described in connection with the present disclosure may be implemented or performed by any combination of a general purpose processor, a DSP, an ASIC, an FPGA, or another programmable logic device, a discrete gate or transistor logic, discrete hardware components, and devices designed to perform the functions described herein. The general purpose processor may be a microprocessor, but alternatively, the processor may be any conventional processor, controller, microcontroller, or state machine. In addition, the processor may be implemented as a combination of computing devices, such as a DSP and a microprocessor, a plurality of microprocessors, one or more microprocessors associated with a DSP core, or a combination of any other devices.

In a firmware and/or software implementation, the techniques may be implemented as commands stored on a computer-readable medium, such as random access memory (RAM), read-only memory (ROM), non-volatile random access memory (NVRAM), programmable read-only memory (PROM), erasable programmable read-only memory (EEPROM), electrically erasable PROM (EEPROM), flash memory, compact disc (CD), or magnetic or marked data storage. The commands may be executable by one or more processors, and may enable the processor(s) to perform certain aspects of the functions described herein.

When implemented in software, the techniques may be stored on or transmitted through a computer-readable medium as one or more commands or code. The computer-readable medium includes both a computer storage medium and a communication medium, including any medium that facilitates transmission of a computer program from one location to another. The storage medium may be any available medium which a computer can access. As a non-limiting example, the computer-readable medium may include RAM, ROM, EEPROM, CD-ROM or another form of optical disc storage, a magnetic disk storage or another form of magnetic storage, or any other medium that may be used to transfer or store desired program code in the form of commands or data structures and that a computer can access. In addition, any access to a computer-readable medium may be appropriately achieved.

For example, when software is transmitted from a website, a server, or another remote source using a coaxial cable, a fiber optic cable, a twisted pair, a digital subscriber line (DSL), or wireless technology such as infrared, radio, and microwave, the coaxial cable, the fiber optic cable, the twisted pair, the digital subscriber line, or wireless technology such as infrared, radio, and microwave are included within the definition of the medium. As used herein, disks and discs include a CD, a laserdisc, an optical disc, a digital versatile disc (DVD), a floppy disk, and a Blu-ray disc, wherein the disks typically reproduce data magnetically, whereas the discs reproduce data optically using a laser. The above combination should also be included within the scope of the computer-readable medium.

A software module may reside in RAM, flash memory, ROM, EPROM, EEPROM, registers, a hard disk, a removable disk, a CD-ROM, or any other form of known storage medium. An exemplary storage medium may be connected to a processor such that the processor can read information from the storage medium or write information to the storage medium. Alternatively, the storage medium may be integrated into the processor. The processor and the storage medium may reside in an ASIC. The ASIC may reside in a user terminal. Alternatively, the processor and the storage medium may reside in the user terminal as separate components.

Although the above embodiments have been described as utilizing aspects of the disclosed subject matter in one or more stand-alone computer systems, the present disclosure is not limited thereto and may be implemented in connection with any computing environment, such as a network or distributed computing environment. Furthermore, aspects of the present disclosure may be implemented on a plurality of processing chips or devices, and storage may be similarly affected across the plurality of devices. Such devices may include PCs, network servers, and portable devices.

According to some embodiments of the present disclosure, various kinds of information associated with genetic information analysis results may be efficiently provided through a plurality of regions included in a user interface.

According to some embodiments of the present disclosure, a user interface capable of interactively inquiring about and searching for a large amount of genetic information analysis results may be provided.

According to some embodiments of the present disclosure, the user interface may include a first browser configured to visualize and search for information about a variant found in a specimen and a second browser configured to search for details about a base sequence, an amino acid sequence, and/or a variant obtained by analysis of the specimen, wherein a user may easily search for the entire base sequence and genetic information using the first browser and the second browser.

According to some embodiments of the present disclosure, the first browser and the second browser may be operated in conjunction with each other such that, when information output from one browser is changed, information output from the other browser is changed in response to the changed information. Under such a configuration, the user may identify linked information through specific input or search, thereby improving convenience in using the browsers.

According to some embodiments of the present disclosure, when different types of variants are output to the first browser, the different types of variants may be output to the first browser using different graphic objects. As a result, the user may intuitively identify the type of a variant that has occurred in the base sequence and easily understand how different types of variants occur.

According to some embodiments of the present disclosure, when variants are densely located in the first browser, graphic processing, such as highlighting a specific variant by a pointer, automatically enlarging a region where variants are dense, or rotating and highlighting a plurality of variants located in the dense region, may be performed. As a result, each variant may be conveniently and accurately identified by the user even though the variants are dense.

According to some embodiments of the present disclosure, when a specific gene included in a list of drivers or a list of genes is selected, a region associated with the selected specific gene, such as a chromosome or gene, may be automatically output to the first browser, and the sequence and/or other variant-related information of a region associated with the selected gene may be automatically output to the second browser. As a result, the user may easily change the information output to the first browser and the second browser by selecting the gene.

The effects of the present disclosure are not limited to those mentioned above, and other unmentioned effects will be clearly understood by a person having ordinary skill in the art to which the present disclosure pertains (referred to as "those skilled in the art") from the claims.

Although the present disclosure has been described herein with reference to some embodiments, various modifications and changes may be made without departing from the scope of the present disclosure understood by a person having ordinary skill in the art to which the present disclosure belongs. In addition, such modifications and changes should be considered to fall within the scope of the appended claims.

What is claimed is:

1. A method of providing genetic information analysis results, performed by at least one hardware processor, the method comprising:

displaying a user interface configured to provide genetic information analysis results for a specimen, wherein the user interface comprises:

a list of genes associated with a specific disease in a first region within the user interface;

a first browser configured to display and search for information regarding a variant obtained from analysis of the specimen in a second region within the user interface; and a second browser configured to search for sequence information obtained from the analysis of the specimen, in a third region within the user interface; and displaying, in response to a user input received through the user interface, interactive response information comprising details of the genetic information analysis results to at least one region within the user interface, wherein in the first browser, labels of genes corresponding to a plurality of mutations detected from the specimen are displayed correspondingly to location of the genes, wherein the displaying the interactive response information comprises:

receiving the user input that selects, among the list of genes displayed in the first region, a gene where a specific mutation is identified;

displaying, on the first browser, a part of the variant information, which corresponds to the selected gene; and displaying, on the second browser, a part of the sequence information, which corresponds to the selected gene, and wherein the displaying the interactive response information further comprises:

displaying, on the part of the variant information, graphic objects in locations corresponding to regions where variants are found in the selected gene;

checking whether the graphic objects are located within a threshold distance, whether more than a threshold number of the graphic objects are located within the threshold distance, or whether a density of the graphic objects is equal to or greater than a threshold value;

determining a dense region where the graphic objects are located within the threshold distance, where more than the threshold number of the graphic objects are located within the threshold distance, or where the density of the graphic objects is equal to or greater than the threshold value; and automatically enlarging or zooming in the dense region for a predetermined period of time.

2. The method according to claim 1, wherein the step of displaying the user interface further comprises displaying a graphic object representing a location of the specific mutation in the region displayed in the second browser, and the method further comprises:

obtaining information regarding the specific mutation from the genetic information analysis results of the specimen; and displaying, in response to receiving user input to select the graphic object, the information regarding the specific mutation, through the second browser.

3. The method according to claim 1,
wherein the step of displaying the interactive response information further comprises:
determining that first amino acid associated with the selected gene where the specific mutation is identified is different from second amino acid translated from a reference sequence, and;
upon the determination, controlling the second browser to display amino acid change information indicating a difference between the first amino acid and the second amino acid, and
wherein the amino acid change information is displayed in a location associated with the specific mutation within the sequence information.

4. The method according to claim 3, further comprises:
in response to determination that the first amino acid associated with the selected gene where the specific mutation is identified is different from second amino acid translated from the reference sequence, automatically enlarging an amino acid region of the first amino acid associated with the selected gene.

5. The method according to claim 1, further comprising:
identifying the specific disease based on a disease code included in patient information; and
wherein the list of genes comprises at least one gene where a mutation is identified from the specimen, the mutation being related to the specific disease.

6. The method according to claim 1,
wherein the list of genes comprises oncogenes related to the specimen and tumor suppressor genes related to the specimen, and
wherein a label of at least one oncogene is displayed in the first region using a first graphic element and a label of at least one tumor suppressor gene is displayed in the first region using a second graphic element.

7. The method according to claim 1,
wherein the step of displaying the user interface further comprises displaying, on the second browser, a graphic object representing a location of the specific mutation within the sequence information displayed in the second browser, and
wherein the step of displaying the interactive response information comprises controlling, in response to receiving user input to select the graphic object, the second browser to enlarge a region of the sequence information associated with the specific mutation.

8. The method according to claim 7, wherein a character associated with at least one of an altered base and an altered amino acid identifier is displayed in the enlarged region of the sequence information.

9. The method according to claim 1, wherein the user interface further comprises:
a comment field,
wherein the method further comprises:
storing at least one of email addresses, contacts, and terminal IP addresses of users participating in each project;
receiving a user comment through the comment field;
identifying a particular project associated with the specimen; and
providing the received user comment to at least one other user who is participating in the particular project.

10. The method according to claim 1,
wherein the step of displaying the user interface further comprises:
displaying first information associated with a plot of tumor mutational burden for the specimen within an additional region of the user interface, and
wherein the first information comprises tumor mutational burden statistics for at least one of a single nucleotide variation for the specimen, an indel for the specimen, and structural variants (SVs) for the specimen.

11. The method according to claim 10, wherein the step of displaying the interactive response information further comprises:
obtaining second information associated with a plot of tumor mutational burden for another specimen; and
displaying the first information and the second information in association with each other.

12. The method according to claim 1, wherein the step of displaying the interactive response information further comprises:
receiving user input to request a comparison of a specific mutation among mutations found in the specimen;
obtaining details of the specific mutation found in another specimen; and
correlating details of the specific mutation found in the specimen with the details of the specific mutation found in the another specimen and displaying the correlation result.

13. The method according to claim 1,
wherein the step of displaying the user interface further comprises displaying an input field in which a gene identifier is entered, and
the method further comprises:
receiving a gene identifier entered through the input field; and
adding a gene corresponding to the received gene identifier to the list of genes.

14. The method according to claim 1, further comprising:
automatically generating a message containing the interactive response information, in response to user input received through the user interface; and
transmitting the message to all of external devices being connected with the at least one processor via a network, so that each external device has immediate access to the interactive response information.

15. A non-transitory computer-readable recording medium storing a computer program being executed by a hardware processor to perform the method according to claim 1.

16. A system comprising:
an information processing system;
a sequencing device;
a DNA library including DNA fragments obtained from one or more patients,
wherein the information processing system collects information from a network of a medical data institution containing DNA information of one or more subjects, to configure the DNA library,
wherein the information processing system comprises a local computer generating network access requests for individual controlled access network accounts, which are managed by the medical data institutions,
wherein the DNA library is loaded into a flow cell to be introduced into the sequencing device,
wherein the sequencing device identifies a base type of each DNA fragment included in the DNA library, and generate marking data including a marking code corresponding to the identified base type,
wherein the sequencing device updates marking data at each cycle by identifying one base included in each DNA fragment, generates a marking code corresponding to the identified base, and further writes the generated marking code to the marking data, wherein at each cycle, the sequencing device generates a single image file representing marking codes generated for all DNA fragments, and the marking data is a set of image files generated at each cycle and is stored in a storage device which the information processing system has access, and wherein the information processing system analyzes a base sequence and outputs, or displays, a genetic information analysis result report including the analyzed results, and the information processing system transmits analysis results to a computing device; and the computing device comprising:

a hardware memory;

a display; and at least one hardware processor connected to the hardware memory, and configured to execute at least one computer-readable program stored in the hardware memory, wherein the at least one hardware processor is configured to:

control the display to display a user interface configured to provide genetic information analysis results for a specimen, wherein the user interface comprises:

a list of genes associated with a specific disease in a first region within the user interface;

a first browser configured to display and search for information regarding a variant obtained from analysis of the specimen in a second region within the user interface; and a second browser configured to search for sequence information obtained from analysis of the specimen in a third region within the user interface; and control the display to display, in response to user input received through the user interface, interactive response information comprising details of the genetic information analysis results to at least one region within the user interface, wherein in the first browser, labels of genes corresponding to a plurality of mutations detected from the specimen are displayed correspondingly to location of the genes, wherein the at least one hardware processor is further configured to:

receive the user input that selects, among the list of genes displayed in the first region, a gene where a specific mutation is identified;

control the display to display, on the first browser, a part of the variant information, which corresponds to the selected gene;

control the display to display, on the second browser, a part of the sequence information, which corresponds to the selected gene;

control the display to display, on the part of the variant information, graphic objects in locations corresponding to regions where variants are found in the selected gene;

check whether the graphic objects are located within a threshold distance, whether more than a threshold number of the graphic objects are located within the threshold distance, or whether a density of the graphic objects is equal to or greater than a threshold value;

determine a dense region where the graphic objects are located within the threshold distance, where more than the threshold number of the graphic objects are located within the threshold distance, or where the density of the graphic objects is equal to or greater than the threshold value; and control the display to automatically enlarge or zoom in the dense region for a predetermined period of time.

17. The system according to claim 16, wherein the at least one hardware processor is configured to:

automatically generate a message containing the interactive response information, in response to user input received through the user interface; and transmit the message to all of external devices being connected with the at least one processor via a network, so that each external device has immediate access to the interactive response information.

18. The method of claim 1, wherein the first browser shows a first graphic element for displaying a label of a gene associated with a mutation associated with causing a disease, and a second graphic element for displaying a label of a gene associated with a mutation associated with suppressing the disease.

19. The method according to claim 1, wherein the displaying the part of the variant information further comprises:

rotationally displaying one graphic object of the graphic objects at a time interval.

* * * * *